(12) United States Patent
Yamaguchi et al.

(10) Patent No.: US 7,252,978 B2
(45) Date of Patent: Aug. 7, 2007

(54) METHOD FOR PRODUCING L-ARGININE

(75) Inventors: Mikiko Yamaguchi, Kawasaki (JP); Hisao Ito, Kawasaki (JP); Yoshiya Gunji, Kawasaki (JP); Hisashi Yasueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/196,232

(22) Filed: Jul. 17, 2002

(65) Prior Publication Data

US 2003/0113899 A1 Jun. 19, 2003

(30) Foreign Application Priority Data

Jul. 25, 2001 (JP) .............................. 2001-224586

(51) Int. Cl.
- C12P 13/04 (2006.01)
- C12N 1/20 (2006.01)
- C12N 15/00 (2006.01)
- C07K 1/00 (2006.01)
- C07H 21/04 (2006.01)

(52) U.S. Cl. .................... 435/106; 435/119; 435/252.1; 435/252.3; 435/252.32; 435/252.33; 435/320.1; 530/350; 536/23.1

(58) Field of Classification Search ................ 435/106, 435/119, 252.1, 252.3, 252.32, 252.33, 320.1; 530/350; 536/23.1
See application file for complete search history.

(56) References Cited

U.S. PATENT DOCUMENTS 5,643,758 A * 7/1997 Guan et al. ................. 435/69.7
5,972,663 A 10/1999 Winterhalter et al.
6,303,381 B1 10/2001 Gunji et al.

FOREIGN PATENT DOCUMENTS

EP 1 016 710 A2 7/2000
WO WO 97/23597 7/1997

OTHER PUBLICATIONS

Attwood et al. Which craft is best in bioinformatics? Comput. Chem. 2001, vol. 25(4), pp. 329-339.*
Ponting, C.P. Issues in predicting protein function from sequence. Brief. Bioinform. Mar. 2001, vol. 2(1), pp. 19-29.*
Vrljic et al. Accession X96471. Dec. 9, 1996.*
Ko et al. Accession AF041436. Jan. 5, 1999.*
Sakanyan et al. Microbiology. Jan. 1996;142 ( Pt 1):99-108 (ABSTRACT).*
Chun et al. Mol Cells. Jun. 30, 1999;9(3):333-7(ABSTRACT).*
Hani et al. J Bacteriol. Apr. 1994;176(7):1865-71 (ABSTRACT).*
Mass. Microbiol Rev. Dec. 1994;58(4):631-40.*
Bellmann et al. Microbiology. Jul. 2001;147(Pt 7):1765-74.*
D. Lim et al., "Nucleotide Sequence of the argR gene of *Escherichia coli* K-12 and isolation of its product, the arginine repressor," *Proc. Natl. Acad. Sci.*, vol. 84, pp. 6697-6701, Oct. 1987.
D. Charlier et al., "Arginine Regulon of *Escherichia coli* K-12," *J. Mol. Biol.* (1992) 226, 367-386.
A. Bellmann et al., "Expression control and specificity of the basic amino acid exporter LysE of *Corynebacterium glutamicum*", *Microbiology*, (2001) 147, 1765-1774.
NCBI Sequence Viewer, Accession No. AF049897, Corynebacterium.
Marina Vrljic et al., "A New Type of Transporter with a new type of cellular function: L-lysine export from *Corynebacterium glutamicum*," *Molecular Microbiology* (1996) 22(5), 815-826.
A. Bellman, et al., "Expression Control and Specificity of the Basic Amino Acid Exporter Lyse of Corynebacterium Glutamicum", Microbiology (2001), 147, 1765-1774.

* cited by examiner

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

L-Arginine is produced by culturing a microorganism which has L-arginine producing ability and has been modified so that expression of lysE gene should be enhanced, such a microorganism further modified so that an arginine repressor should not function normally, or such a microorganism further modified so that intracellular activity of an enzyme in L-arginine biosynthetic pathway should be enhanced in a medium to produce and accumulate L-arginine in the medium and collecting the L-arginine from the medium.

5 Claims, 5 Drawing Sheets

SEQUENCE LISTING

```
<160> NUMBER OF SEQ ID NOS: 35

<210> SEQ ID NO 1
<211> LENGTH: 32
<212> TYPE: DNA
<213> ORGANISM: Artificial Sequence
<220> FEATURE:
<223> OTHER INFORMATION: Synthetic DNA

<400> SEQUENCE: 1
cccgttaact gcttgaaacc caggacaata ac                                 32

<210> SEQ ID NO 2
<211> LENGTH: 30
<212> TYPE: DNA
<213> ORGANISM: Artificial Sequence
<220> FEATURE:
<223> OTHER INFORMATION: Synthetic DNA

<400> SEQUENCE: 2
cccgttaaca tgtacttcag aaaagattag                                    30

<210> SEQ ID NO 3
<211> LENGTH: 26
<212> TYPE: DNA
<213> ORGANISM: Artificial Sequence
<220> FEATURE:
<223> OTHER INFORMATION: Synthetic DNA
```

```
<400> SEQUENCE: 3
gatatctacg tgccgatcaa cgtctc                                          26

<210> SEQ ID NO 4
<211> LENGTH: 25
<212> TYPE: DNA
<213> ORGANISM: Artificial Sequence
<220> FEATURE:
<223> OTHER INFORMATION: Synthetic DNA

<400> SEQUENCE: 4
aggccttttt ttaaggcagt tattg                                           25

<210> SEQ ID NO 5
<211> LENGTH: 4447
<212> TYPE: DNA
<213> ORGANISM: Brevibacterium lactofermentum

<400> SEQUENCE: 5
aagcttgtct acgtctgatg ctttgaatcg gacggacttg ccgatcttgt atgcggtgat       60
ttttccctcg tttgcccact ttttaatggt ggccggggtg agagctacgc gggcggcgac      120
ctgctgcgct gtgatccaat attcggggtc gttcactggt tccccttttct gatttctggc     180 atagaagaac ccccgtgaac tgtgtggttc cggggggttgc tgattttttgc gagacttctc    240 gcgcaattcc ctagcttagg tgaaaacacc atgaaacact agggaaacac ccatgaaaca      300
cccattaggg cagtagggcg gcttcttcgt ctagggcttg catttgggcg gtgatctggt      360
ctttagcgtg tgaaagtgtg tcgtaggtgg cgtgctcaat gcactcgaac gtcacgtcat      420
ttaccgggtc acggtgggca aagagaacta gtgggttaga cattgttttc ctcgttgtcg      480
gtggtggtga gcttttctag ccgctcggta acgcggcga tcatgaactc ttggaggttt       540
tcaccgttct gcatgcctgc gcgcttcatg tcctcacgta gtgccaaagg aacgcgtgcg     600
gtgaccacga cgggcttagc ctttgcctgc gcttctagtg cttcgatggt ggcttgtgcc     660
tgcgcttgct gcgcctgtag tgcctgttga gcttcttgta gttgctgttc tagctgtgcc     720
ttggttgcca tgcttaaaga ctctagtagc tttcctgcga tatgtcatgc gcatgcgtag    780
caaacattgt cctgcaactc attcattatg tgcagtgctc ctgttactag tcgtacatac    840
tcatatttac ctagtctgca tgcagtgcat gcacatgcag tcatgtcgtg ctaatgtgta    900
aaacatgtac atgcagattg ctgggggtgc aggggcgga gccaccctgt ccatgcgggg    960
tgtgggcctt gccccgccgg tacagacagt gagcaccggg gcacctagtc gcggataccc    1020
cccctaggta tcggacacgt aaccctccca tgtcgatgca aatctttaac attgagtacg    1080
ggtaagctgg cacgcatagc caagctaggc ggccaccaaa caccactaaa aattaatagt    1140
ccctagacaa dacaaacccc cgtgcgagct accaactcat atgcacgggg gccacataac    1200
ccgaaggggt ttcaattgac aaccatagca ctagctaaga caacgggcac aacacccgca    1260
caaactcgca ctgcgcaacc ccgcacaaca tcgggtctag gtaacactga aatagaagtg    1320
aacacctcta aggaaccgca ggtcaatgag ggttctaagg tcactcgcgc tagggcgtgg    1380
cgtaggcaaa acgtcatgta caagatcacc aatagtaagg ctctggcggg gtgccatagg    1440
tggcgcaggg acgaagctgt tgcggtgtcc tggtcgtcta acggtgcttc gcagtttgag    1500
ggtctgcaaa actctcactc tcgctggggg tcacctctgg ctgaattgga agtcatgggc    1560
gaacgccgca ttgagctggc tattgctact aagaatcact ggcggcggg tggcgcgctc    1620 atgatgtttg tgggcactgt tcgacacaac cgctcacagt catttgcgca ggttgaagcg    1680
```

```
ggtattaaga ctgcgtactc ttcgatggtg aaaacatctc agtggaagaa agaacgtgca    1740
cggtacgggg tggagcacac ctatagtgac tatgaggtca cagactcttg ggcgaacggt    1800
tggcacttgc accgcaacat gctgttgttc ttggatcgtc cactgtctga cgatgaactc    1860
aaggcgtttg aggattccat gttttcccgc tggtctgctg gtgtggttaa ggccggtatg    1920
gacgcgccac tgcgtgagca cggggtcaaa cttgatcagg tgtctacctg gggtggagac    1980
gctgcgaaaa tggcaaccta cctcgctaag ggcatgtctc aggaactgac tggctccgct    2040
actaaaaccg cgtctaaggg gtcgtacacg ccgtttcaga tgttggatat gttggccgat    2100
caaagcgacg ccggcgagga tatggacgct gttttggtgg ctcggtggcg tgagtatgag    2160
gttggttcta aaaacctgcg ttcgtcctgg tcacgtgggg ctaagcgtgc tttgggcatt    2220
gattacatag acgctgatgt acgtcgtgaa atggaagaag aactgtacaa gctcgccggt    2280
ctggaagcac cggaacgggt cgaatcaacc cgcgttgctg ttgctttggt gaagcccgat    2340
gattggaaac tgattcagtc tgatttcgcg gttaggcagt acgttctaga ttgcgtggat    2400
aaggctaagg acgtggccgc tgcgcaacgt gtcgctaatg aggtgctggc aagtctgggt    2460
gtggattcca ccccgtgcat gatcgttatg gatgatgtgg acttggacgc ggttctgcct    2520
actcatgggg acgctactaa gcgtgatctg aatgcggcgg tgttcgcggg taatgagcag    2580
actattcttc gcacccacta aaagcggcat aaaccccgtt cgatattttg tgcgatgaat    2640
ttatggtcaa tgtcgcgggg gcaaactatg atgggtcttg ttgttgacaa tggctgatttt   2700 catcaggaat ggaactgtca tgctgttatg tgcctggctc ctaatcaaag ctggggacaa    2760
tgggttgccc cgttgatctg atctagttcg gattggcggg gcttcactgt atctgggggt    2820
ggcatcgtga atagattgca caccgtagtg gcagtgtgc acaccatagt gggcatgagt     2880
aatacctacg cgcgcgtggg ctagggctta acgcgcgttt tgccgtgctg cggggcatac    2940
gttagcgcat acgcttttttt ctgtgaaacc tttttgtgtt ttgtttcgt gttggtttcc    3000 tttctgttgg cggggcaact taacgcctgc ggggggtggtt gttgacgtta acggggtag    3060 ttttttattcc cctagtggtt tttcagtacg acaatcgaga aagacctgtt tcagccagtt    3120
cgggtcatgt tcgtcggtat ggccacgtgc atagcgacca gttttcgagt tcactgggat    3180
ttttggtgca tcgaacaaga tgtaggacaa tgccggtttct aggtctactt tttgctttat    3240
gccgtacaag ccccgtgggt attcagcgat tgattccaag gcggcttccc agtcctgttt    3300
tgtgaaggac tggcttagtt ctaggtctgt gtctgggtag tactgcttgt ttgtgtaagc    3360
gccgttggtg ctcattgatg attcctttga agtgtttgga gttcggctag tagtgcggcg    3420
tatggtgctg ctttttgctc gtgatagctc gccttggcta tgaggtcggc taggtaggtt    3480
tccggggtgc ctaggttgcg taggtctagc aaatcccggt atgtggcctg tgcgctgcgc    3540
tggtggtgca tacagtcgtt aagctgggct tttacgtctg cgatgcggtg gcggttaggc    3600
atgttggtgt gcttcttcca agtactcacg ggcgggtttt gtgtatgcct ggcgtgatgc    3660
ttctttgagc tgttggagtt ccgcttggag tgcgggtagt tcgtccgcga actgcttgtg    3720
gtactcgtat ttctcttgtt cctgggcgat agcatttgcg ttgaattgca gggcggtgag    3780
ttcgtccacg cgtcgttttg ctgcgttggt catggtggcg tgccatttgc ggttgtggac    3840
gcggggttca aggttgcgca cggctgcttc ggctaggttg gtggctgctt ttttcagtgc    3900
tcgggcttcc cgttcctcgt ccaacgagag cacctttggt ttgttggctt cggctagttt    3960
ttgcttctcc gctttgatga gttggtcaac ttcgtgttgg gagaggtcgt ttttcacgat    4020
```

-continued

```
gcgtcgaatg tggtcgttgt gggtgctgag ttggtgtgag aggtagtggg gttctgggat    4080
ttcggcgagt tggtcgaggt tggtgtagtg cgggttgcgg cctggttggt tgggttcgct    4140
ggggaggtcg atgtatccgg ttgagtctcc ggcgtggttg aagtgaatta ggcgttggta    4200
gccgtattcc tggttgggga ggtacgacag aatgaggaag tttggtgctt ctcctgcaat    4260
gagtcgtgcg tgttcgtagt tcggtactgg gtcgtgctcg gggagaatgt tcttttgggt    4320
catggcttct ctttctgttg ctctgtaagt ccgtatgtgg gcatgggaaa gccccggcaa    4380 cccctttgggt caaccggggc tagatagtcg cttagaatgg cttctaggct gcgtctcggg    4440
gtgtggc                                                              4447
```

<210> SEQ ID NO 6
<211> LENGTH: 4447
<212> TYPE: DNA
<213> ORGANISM: Brevibacterium lactofermentum
<220> FEATURE:
<221> NAME/KEY: CDS
<222> LOCATION: (1318)..(2598)
<223> OTHER INFORMATION:

<400> SEQUENCE: 6

```
aagcttgtct acgtctgatg ctttgaatcg dacggacttg ccgatcttgt atgcggtgat      60 ttttcccctcg tttgcccact ttttaatggt ggccggggtg agagctacgc gggcggcgac    120
ctgctgcgct gtgatccaat attcggggtc gttcactggt tccccttttct gatttctggc    180 atagaagaac ccccgtgaac tgtgtggttc cggggggttgc tgattttttgc gagacttctc    240 gcgcaattcc ctagcttagg tgaaaacacc atgaaacact agggaaacac ccatgaaaca    300
cccattaggg cagtagggcg gcttcttcgt ctagggcttg catttgggcg gtgatctggt    360
ctttagcgtg tgaaagtgtg tcgtaggtgg cgtgctcaat gcactcgaac gtcacgtcat    420
ttaccgggtc acggtgggca aagagaacta gtgggttaga cattgttttc ctcgttgtcg    480
gtggtggtga gcttttctag ccgctcggta aacgcggcga tcatgaactc ttggaggttt    540
tcaccgttct gcatgcctgc gcgcttcatg tcctcacgta gtgccaaagg aacgcgtgcg    600
gtgaccacga cgggcttagc ctttgcctgc gcttctagtg cttcgatggt ggcttgtgcc    660
tgcgcttgct gcgcctgtag tgcctgttga gcttcttgta gttgctgttc tagctgtgcc    720
ttggttgcca tgctttaaga ctctagtagc tttcctgcga tatgtcatgc gcatgcgtag    780
caaacattgt cctgcaactc attcattatg tgcagtgctc ctgttactag tcgtacatac    840
tcatatttac ctagtctgca tgcagtgcat gcacatgcag tcatgtcgtg ctaatgtgta    900
aaacatgtac atgcagattg ctggggtgc aggggcgga ccaccctgt ccatgcgggg       960 tgtgggctt gccccgccgg tacagacagt gagcaccggg gcacctagtc gcggataccc     1020 ccctaggta tcggacacgt aaccctccca tgtcgatgca aatctttaac attgagtacg     1080
ggtaagctgg cacgcatagc caagctaggc ggccaccaaa caccactaaa aattaatagt    1140
tcctagacaa gacaaacccc cgtgcgagct accaactcat atgcacgggg gccacataac    1200 ccgaagggt ttcaattgac aaccatagca ctagctaaga caacgggcac aacatccgca     1260
caaactcgca ctgcgcaacc ccgcacaaca tcgggtctag gtaacactga aatagaa       1317
```

```
gtg aac acc tct aag gaa ccg cag gtc aat gag ggt tct aag gtc act     1365
Val Asn Thr Ser Lys Glu Pro Gln Val Asn Glu Gly Ser Lys Val Thr
 1                5                 10                  15 cgc gct agg gcg tgg cgt agg caa aac gtc atg tac aag atc acc aat    1413
Arg Ala Arg Ala Trp Arg Arg Gln Asn Val Met Tyr Lys Ile Thr Asn
             20                  25                  30
```

-continued

| | |
|---|---:|
| agt aag gct ctg gcg ggg tgc cat agg tgg cgc agg gac gaa gct gtt<br>Ser Lys Ala Leu Ala Gly Cys His Arg Trp Arg Arg Asp Glu Ala Val<br>    35                        40                        45 | 1461 |
| gcg gtg tcc tgg tcg tct aac ggt gct tcg cag ttt gag ggt ctg caa<br>Ala Val Ser Trp Ser Ser Asn Gly Ala Ser Gln Phe Glu Gly Leu Gln<br>50                        55                        60 | 1509 |
| aac tct cac tct cgc tgg ggg tca tct ctg gct gaa ttg gaa gtc atg<br>Asn Ser His Ser Arg Trp Gly Ser Ser Leu Ala Glu Leu Glu Val Met<br>65                        70                        75                        80 | 1557 |
| ggc gaa cgc cgc att gag ctg gct att gct act aag aat cac ttg gcg<br>Gly Glu Arg Arg Ile Glu Leu Ala Ile Ala Thr Lys Asn His Leu Ala<br>                  85                        90                        95 | 1605 |
| gcg ggt ggc gcg ctc atg atg ttt gtg ggc act gtt cga cac aac cgc<br>Ala Gly Gly Ala Leu Met Met Phe Val Gly Thr Val Arg His Asn Arg<br>            100                        105                      110 | 1653 |
| tca cag tca ttt gcg cag gtt gaa gcg ggt att aag act gcg tac tct<br>Ser Gln Ser Phe Ala Gln Val Glu Ala Gly Ile Lys Thr Ala Tyr Ser<br>              115                        120                      125 | 1701 |
| tcg atg gtg aaa aca tct cag tgg aag aaa gaa cgt gca cgg tac ggg<br>Ser Met Val Lys Thr Ser Gln Trp Lys Lys Glu Arg Ala Arg Tyr Gly<br>130                        135                      140 | 1749 |
| gtg gag cac acc tat agt gac tat gag gtc aca gac tct tgg gcg aac<br>Val Glu His Thr Tyr Ser Asp Tyr Glu Val Thr Asp Ser Trp Ala Asn<br>145                        150                      155              160 | 1797 |
| ggt tgg cac ttg cac cgc aac atg ctg ttg ttc ttg gat cgt cca ctg<br>Gly Trp His Leu His Arg Asn Met Leu Leu Phe Leu Asp Arg Pro Leu<br>                  165                      170                      175 | 1845 |
| tct gac gat gaa ctc aag gca ttt gag gat tcc atg ttt tcc cgc tgg<br>Ser Asp Asp Glu Leu Lys Ala Phe Glu Asp Ser Met Phe Ser Arg Trp<br>180                        185                      190 | 1893 |
| tct gct ggt gtg gtt aag gcc ggt atg gac gcg cca ctg cgt gag cac<br>Ser Ala Gly Val Val Lys Ala Gly Met Asp Ala Pro Leu Arg Glu His<br>              195                        200                      205 | 1941 |
| ggg gtc aaa ctt gat cag gtg tct acc tgg ggt gga gac gct gcg aaa<br>Gly Val Lys Leu Asp Gln Val Ser Thr Trp Gly Gly Asp Ala Ala Lys<br>210                        215                      220 | 1989 |
| atg gca acc tac ctc gct aag ggc atg tct cag gaa ctg act ggc tcc<br>Met Ala Thr Tyr Leu Ala Lys Gly Met Ser Gln Glu Leu Thr Gly Ser<br>225                        230                      235              240 | 2037 |
| gct act aaa acc gcg tct aaa ggg tcg tac acg ccg ttt cag atg ttg<br>Ala Thr Lys Thr Ala Ser Lys Gly Ser Tyr Thr Pro Phe Gln Met Leu<br>                  245                      250                      255 | 2085 |
| gat atg ttg gcc gat caa agc gac gcc ggc gag gat atg gac gct gtt<br>Asp Met Leu Ala Asp Gln Ser Asp Ala Gly Glu Asp Met Asp Ala Val<br>260                        265                      270 | 2133 |
| ttg gtg gct cgg tgg cgt gag tat gag gtt ggt tct aaa aac ctg cgt<br>Leu Val Ala Arg Trp Arg Glu Tyr Glu Val Gly Ser Lys Asn Leu Arg<br>              275                        280                      285 | 2181 |
| tcg tct tgg tca cgt ggg gct aag cgt gct ttg ggc att gat tac ata<br>Ser Ser Trp Ser Arg Gly Ala Lys Arg Ala Leu Gly Ile Asp Tyr Ile<br>290                        295                      300 | 2229 |
| gac gct gat gta cgt cgt gaa atg gaa gaa gaa ctg tac aag ctc gcc<br>Asp Ala Asp Val Arg Arg Glu Met Glu Glu Glu Leu Tyr Lys Leu Ala<br>305                        310                      315              320 | 2277 |
| ggt ctg gaa gca ccg gaa cgg gtc gaa tca acc cgc gtt gct gtt gct<br>Gly Leu Glu Ala Pro Glu Arg Val Glu Ser Thr Arg Val Ala Val Ala<br>                  325                      330                      335 | 2325 |
| ttg gtg aag ccc gat gat tgg aaa ctg att cag tct gat ttc gcg gtt<br>Leu Val Lys Pro Asp Asp Trp Lys Leu Ile Gln Ser Asp Phe Ala Val | 2373 |

-continued

|  | 340 | 345 | 350 |  |
|---|---|---|---|---|
| agg cag tac gtt cta gat tgc gtg gat aag gct aag gac gtg gcc gct | | | | 2421 |
| Arg Gln Tyr Val Leu Asp Cys Val Asp Lys Ala Lys Asp Val Ala Ala | | | | |
| 355 | | 360 | 365 | |
| gcg caa cgt gtc gct aat gag gtg ctg gca agt ctg ggt gtg gat tcc | | | | 2469 |
| Ala Gln Arg Val Ala Asn Glu Val Leu Ala Ser Leu Gly Val Asp Ser | | | | |
| 370 | | 375 | 380 | |
| acc ccg tgc atg atc gtt atg gat gat gtg gac ttg gac gcg gtt ctg | | | | 2517 |
| Thr Pro Cys Met Ile Val Met Asp Asp Val Asp Leu Asp Ala Val Leu | | | | |
| 385 | 390 | 395 | 400 | |
| cct act cat ggg gac gct act aag cgt gat ctg aat gcg gcg gtg ttc | | | | 2565 |
| Pro Thr His Gly Asp Ala Thr Lys Arg Asp Leu Asn Ala Ala Val Phe | | | | |
| | 405 | 410 | 415 | |
| gcg ggt aat gag cag act att ctt cgc acc cac taaaagcggc ataaacccg | | | | 2618 |
| Ala Gly Asn Glu Gln Thr Ile Leu Arg Thr His | | | | |
| 420 | 425 | | | | ttcgatattt tgtgcgatga atttatggtc aatgtcgcgg gggcaaacta tgatgggtct 2678
tgttgttgac aatggctgat tcatcagga atggaactgt catgctgtta tgtgcctggc 2738
tcctaatcaa agctggggac aatgggttgc cccgttgatc tgatctagtt cggattggcg 2798
gggcttcact gtatctgggg gtggcatcgt gaatagattg cacaccgtag tgggcagtgt 2858
gcacaccata gtgggcatga gtaataccta cgcgcgcgtg ggctagggct taacgcgcgt 2918
tttgccgtgc tgcgggcat acgttagcgc atacgctttt ttctgtgaaa ccttttttgtg 2978
ttgttgtttc gtgttggttt cctttctgtt ggcggggcaa cttaacgcct gcggggtgg 3038
ttgttgacgt taacgggggt agttttattt ccctagtgg tttttcagta cgacaatcga 3098
gaaagacctg tttcagccag ttcgggtcat gttcgtcggt atggccacgt gcatagcgac 3158
cagttttcga gttcactggg attttttggtg catcaaacaa gatgtaggac aatgcggttt 3218
ctaggtctac ttttttgcttt atgccgtaca agccccgtgg gtattcagcg attgattcca 3278
aggcggcttc ccagtcctgt tttgtgaagg actggcttag ttctaggtct gtgtctgggt 3338
agtactgctt gtttgtgtaa gcgccgttgg tgctcattga tgattccttt gaagtgtttg 3398
gagttcggct agtagtgcgg cgtatggtgc tgcttttttgc tcgtgatagc tcgccttggc 3458
tatgaggtcg gctaggtagg tttccggggt gcctaggttg cgtaggtcta gcaaatcccg 3518
gtatgtggcc tgtgcgctgc gctggtggtg catacagtcg ttaagctggg cttttacgtc 3578
tgcgatgcgg tggcgttag gcatgttggt gtgcttcttc caagtactca cgggcgggtt 3638
ttgtgtatgc ctggcgtgat gcttctttga gctgttggag ttccgcttgg agtgcgggta 3698
gttcgtccgc gaactgcttg tggtactcgt atttctcttg ttcctgggcg atagcatttg 3758
cgttgaattg caggcggtg agttcgtcca cgcgtcgttt tgctgcgttg gtcatggtgg 3818
cgtgccattt gcggttgtgg acgcggggtt caaggttgcg cacggctgct tcggctaggt 3878
tggtggctgc ttttttcagt gctcgggctt cccgttcctc gtccaacgag agcacctttg 3938
gtttgttggc ttcggctagt ttttgcttct ccgctttgat gagttggtca acttcgtgtt 3998
gggagaggtc gttttttcacg atgcgtcgaa tgtggtcgtt gtgggtgctg agttggtgtg 4058
agaggtagtg gggttctggg atttcggcga gttggtcgag gttggtgtag tgcgggttgc 4118
ggcctggttg gttgggttcg ctggggaggt cgatgtatcc ggttgagtct ccggcgtggt 4178
tgaagtgaat taggcgttgg tagccgtatt cctggttggg gaggtacgac agaatgagga 4238
agtttggtgc ttctccctgca atgagtcgtg cgtgttcgta gttcggtact gggtcgtgct 4298
cggggagaat gttcttttgg gtcatggctt ctctttctgt tgctctgtaa gtccgtatgt 4358

```
gggcatggga aagccccggc aacccttttgg gtcaaccggg gctagatagt cgcttagaat    4418
ggcttctagg ctgcgtctcg gggtgtggc                                      4447
```

<210> SEQ ID NO 7
<211> LENGTH: 427
<212> TYPE: PRT
<213> ORGANISM: Brevibacterium lactofermentum

<400> SEQUENCE: 7

```
Val Asn Thr Ser Lys Glu Pro Gln Val Asn Glu Gly Ser Lys Val Thr
1               5                   10                  15

Arg Ala Arg Ala Trp Arg Arg Gln Asn Val Met Tyr Lys Ile Thr Asn
            20                  25                  30

Ser Lys Ala Leu Ala Gly Cys His Arg Trp Arg Arg Asp Glu Ala Val
        35                  40                  45

Ala Val Ser Trp Ser Ser Asn Gly Ala Ser Gln Phe Glu Gly Leu Gln
    50                  55                  60

Asn Ser His Ser Arg Trp Gly Ser Ser Leu Ala Glu Leu Glu Val Met
65                  70                  75                  80

Gly Glu Arg Arg Ile Glu Leu Ala Ile Ala Thr Lys Asn His Leu Ala
                85                  90                  95

Ala Gly Gly Ala Leu Met Met Phe Val Gly Thr Val Arg His Asn Arg
            100                 105                 110

Ser Gln Ser Phe Ala Gln Val Glu Ala Gly Ile Lys Thr Ala Tyr Ser
        115                 120                 125

Ser Met Val Lys Thr Ser Gln Trp Lys Lys Glu Arg Ala Arg Tyr Gly
    130                 135                 140

Val Glu His Thr Tyr Ser Asp Tyr Glu Val Thr Asp Ser Trp Ala Asn
145                 150                 155                 160

Gly Trp His Leu His Arg Asn Met Leu Leu Phe Leu Asp Arg Pro Leu
                165                 170                 175

Ser Asp Asp Glu Leu Lys Ala Phe Glu Asp Ser Met Phe Ser Arg Trp
            180                 185                 190

Ser Ala Gly Val Val Lys Ala Gly Met Asp Ala Pro Leu Arg Glu His
        195                 200                 205

Gly Val Lys Leu Asp Gln Val Ser Thr Trp Gly Asp Ala Ala Lys
    210                 215                 220

Met Ala Thr Tyr Leu Ala Lys Gly Met Ser Gln Glu Leu Thr Gly Ser
225                 230                 235                 240

Ala Thr Lys Thr Ala Ser Lys Gly Ser Tyr Thr Pro Phe Gln Met Leu
                245                 250                 255

Asp Met Leu Ala Asp Gln Ser Asp Ala Gly Glu Asp Met Asp Ala Val
            260                 265                 270

Leu Val Ala Arg Trp Arg Glu Tyr Glu Val Gly Ser Lys Asn Leu Arg
        275                 280                 285

Ser Ser Trp Ser Arg Gly Ala Lys Arg Ala Leu Gly Ile Asp Tyr Ile
    290                 295                 300

Asp Ala Asp Val Arg Arg Glu Met Glu Glu Leu Tyr Lys Leu Ala
305                 310                 315                 320

Gly Leu Glu Ala Pro Glu Arg Val Glu Ser Thr Arg Val Ala Val Ala
                325                 330                 335

Leu Val Lys Pro Asp Asp Trp Lys Leu Ile Gln Ser Asp Phe Ala Val
            340                 345                 350
```

```
Arg Gln Tyr Val Leu Asp Cys Val Asp Lys Ala Lys Asp Val Ala Ala
        355                 360                 365

Ala Gln Arg Val Ala Asn Glu Val Leu Ala Ser Leu Gly Val Asp Ser
    370                 375                 380

Thr Pro Cys Met Ile Val Met Asp Asp Val Asp Leu Asp Ala Val Leu
385                 390                 395                 400

Pro Thr His Gly Asp Ala Thr Lys Arg Asp Leu Asn Ala Ala Val Phe
                405                 410                 415

Ala Gly Asn Glu Gln Thr Ile Leu Arg Thr His
            420                 425

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
aaacccgggc tacgtctgat gctttgaatc                                30

<210> SEQ ID NO 9
<211> LENGTH: 23
<212> TYPE: DNA
<213> ORGANISM: Artificial Sequence
<220> FEATURE:
<223> OTHER INFORMATION: Synthetic DNA

<400> SEQUENCE: 9
ttggtgcatc aaacaagatg tag                                       23

<210> SEQ ID NO 10
<211> LENGTH: 28
<212> TYPE: DNA
<213> ORGANISM: Artificial Sequence
<220> FEATURE:
<223> OTHER INFORMATION: Synthetic DNA

<400> SEQUENCE: 10
ttttcccggg agcttgccac accccgag                                  28

<210> SEQ ID NO 11
<211> LENGTH: 27
<212> TYPE: DNA
<213> ORGANISM: Artificial Sequence
<220> FEATURE:
<223> OTHER INFORMATION: Synthetic DNA

<400> SEQUENCE: 11
tgtcctacat cttgtttgat gcaccaa                                   27

<210> SEQ ID NO 12
<211> LENGTH: 24
<212> TYPE: DNA
<213> ORGANISM: Artificial Sequence
<220> FEATURE:
<223> OTHER INFORMATION: Synthetic DNA

<400> SEQUENCE: 12
gaggttttca ccgttctgca tgcc                                      24

<210> SEQ ID NO 13
<211> LENGTH: 23
<212> TYPE: DNA
```

```
<213> ORGANISM: Artificial Sequence
<220> FEATURE:
<223> OTHER INFORMATION: Synthetic DNA

<400> SEQUENCE: 13
aactcaccgc cctgcaattc aac                                              23

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14
gcctaccgcg gcaaagaagt ggcag                                            25

<210> SEQ ID NO 15
<211> LENGTH: 25
<212> TYPE: DNA
<213> ORGANISM: Artificial Sequence
<220> FEATURE:
<223> OTHER INFORMATION: Synthetic DNA

<400> SEQUENCE: 15
gccttgaact aggggcgctt taagt                                            25

<210> SEQ ID NO 16
<211> LENGTH: 4235
<212> TYPE: DNA
<213> ORGANISM: Brevibacterium flavum
<220> FEATURE:
<221> NAME/KEY: CDS
<222> LOCATION: (1852)..(2364)
<223> OTHER INFORMATION:

<400> SEQUENCE: 16
aaacccgggt tttcttctgc aactcgggcg ccgaagcaaa cgaggctgct ttcaagattg        60
cacgcttgac tggtcgttcc cggattctgg ctgcagttca tggtttccac ggccgcacca       120
tgggttccct cgcgctgact ggccagccag acaagcgtga agcgttcctg ccaatgccaa       180
gcggtgtgga gttctaccct tacggcgaca ccgattactt gcgcaaaatg gtagaaacca       240
acccaacgga tgtggctgct atcttcctcg agccaatcca gggtgaaacg ggcgttgttc       300
cagcacctga aggattcctc aaggcagtgc gcgagctgtg cgatgagtac ggcatcttga       360
tgatcaccga tgaagtccag actggcgttg gccgtaccgg cgatttcttt gcacatcagc       420
acgatggcgt tgttcccgat gtggtgacca tggccaaggg acttggcggc ggtcttccca       480
tcggtgcttg tttggccact ggccgtgcag ctgaattgat gaccccaggc aagcacggca       540
ccactttcgg tggcaaccca gttgcttgtg cagctgccaa ggcagtgctg tctgttgtcg       600
atgacgcttt ctgcgcagaa gttacccgca agggcgagct gttcaaggta cttcttgcca       660
aggttgacgg cgttgtagac gtccgtggca ggggcttgat gttgggcgtg gtgctggagc       720
gcgacgtcgc aaagcaagct gttcttgatg gttttaagca cggcgttatt ttgaatgcac       780
cggcggacaa cattatccgt ttgaccccgc cgctggtgat caccgacgaa gaaatcgcag       840
acgcagtcaa ggctattgcc gagacaatcg cataaaggac ttaaactat gacttcacaa       900 ccacaggttc gccatttcct ggctgatgat gatctcaccc ctgcagagca ggcagaggtt       960 ttgacccctag ccgcaaagct caaggcagcg ccgttttcgg agcgtccact cgagggacca      1020
aagtccgttg cagttctttt tgataagact tcaactcgta ctcgcttctc cttcgacgcg      1080
```

```
ggcatcgctc atttgggtgg acatgccatc gtcgtggatt ccggcagctc acagatgggt     1140
aagggcgaga ccctgcagga caccgcagct gtattgtccc gctacgtgga agcaattgtg     1200
tggcgcacct acgcacacag caatttccac gccatggcgg agacgtccac tgtgccgctg     1260
gtgaactcct tgtccgatga tctgcaccca tgccagattc tggctgatct gcagaccatc     1320
gtggaaaacc tcagccctga agaaggccca gcaggcctta agggtaagaa ggctgtgtac     1380
ctgggcgatg cgacaacaa catggccaac tcctacatga ttggctttgc caccgcgggc     1440
atggatattt ccatcatcgc tcctgaaggg ttccagcctc gtgcggaatt cgtggagcgc     1500
gcggaaaagc gtggccagga accggcgcg aaggttgttg tcaccgacag cctcgacgag     1560
gttgccggcg ccgatgttgt catcaccgat acctgggtat ccatgggtat ggaaaacgac     1620
ggcatcgatc gcaccacacc tttcgttcct taccaggtca acgatgaggt catggcgaaa     1680
gctaacgacg cgccatcttt cctgcactgc cttcctgcct accgcggcaa agaagtggca     1740
gcctccgtga ttgatggacc agcgtccaaa gttttcgatg aagcagaaaa ccgcctccac     1800
gctcagaaag cactgctggt gtggctgctg ccaaccagc cgaggtaaga c atg tct     1857
                                                         Met Ser
                                                           1 ctt ggc tca acc ccg tca aca ccg gaa aac tta aat ccc gtg act cgc     1905
Leu Gly Ser Thr Pro Ser Thr Pro Glu Asn Leu Asn Pro Val Thr Arg
        5                  10                  15 act gca cgc caa gct ctc att ttg cag att ttg gac aaa caa aaa gtc     1953
Thr Ala Arg Gln Ala Leu Ile Leu Gln Ile Leu Asp Lys Gln Lys Val
 20                  25                  30 acc agc cag gta caa ctg tct gaa ttg ctg ctg gat gaa ggc atc gat     2001
Thr Ser Gln Val Gln Leu Ser Glu Leu Leu Leu Asp Glu Gly Ile Asp
35                  40                  45                  50 atc acc cag gcc acc ttg tcc cgg gat ctc gat gaa ctc ggt gca cgc     2049
Ile Thr Gln Ala Thr Leu Ser Arg Asp Leu Asp Glu Leu Gly Ala Arg
                55                  60                  65 aag gtt cgc ccc gat ggg gga cgc gcc tac tac gcg gtc ggc cca gta     2097
Lys Val Arg Pro Asp Gly Gly Arg Ala Tyr Tyr Ala Val Gly Pro Val
         70                  75                  80 gat agc atc gcc cgc gaa gat ctc cgg ggt ccg tcg gag aag ctg cgc     2145
Asp Ser Ile Ala Arg Glu Asp Leu Arg Gly Pro Ser Glu Lys Leu Arg
     85                  90                  95 cgc atg ctt gat gaa ctg ctg gtt tct aca gat cat tcc ggc aac atc     2193
Arg Met Leu Asp Glu Leu Leu Val Ser Thr Asp His Ser Gly Asn Ile
100                 105                 110 gcg atg ctg cgc acc ccg ccg gga gct gcc cag tac ctg gca agt ttc     2241
Ala Met Leu Arg Thr Pro Pro Gly Ala Ala Gln Tyr Leu Ala Ser Phe
115                 120                 125                 130 atc gat agg gtg ggg ctg aaa gaa gtc gtt ggc acc atc gct ggc gat     2289
Ile Asp Arg Val Gly Leu Lys Glu Val Val Gly Thr Ile Ala Gly Asp
                135                 140                 145 gac acc gtt ttt gtt ctc gcc cgt gat ccg ctc aca ggt aaa gaa cta     2337
Asp Thr Val Phe Val Leu Ala Arg Asp Pro Leu Thr Gly Lys Glu Leu
            150                 155                 160 ggt gaa tta ctc agc ggg cgc acc act taaagcgccc ctagttcaag            2384
Gly Glu Leu Leu Ser Gly Arg Thr Thr
            165                 170 gcttgttaat cgcttgttaa tgcaggcagg taaggtataa cccgagtgtt ttttcgagga    2444
ataccaaccc tttcaacaca ataattttct ttaaacatcc ttgctgtcca ccacggctgg    2504
caaggaactt aaaatgaagg agcacacctc atgactaacc gcatcgttct tgcatactcc    2564
```

-continued

```
ggcggtctgg acaccactgt ggcaattcca tacctgaaga agatgattga tggtgaagtc   2624
atcgcagttt ctctcgacct gggccagggt ggagagaaca tggacaacgt tcgccagcgt   2684
gcattggatg ccggtgcagc tgagtccatc gttgttgatg caaaggatga ggttcgctga g   2744
gagtactgcc tgccaaccat caaggcaaac ggcatgtaca tgaagcagta cccactggtt   2804
tctgcaatct cccgcccact gatcgtcaag cacctcgttg aggctggcaa gcagttcaac   2864
ggtacccacg ttgcacacgg ctgcactggt aagggcaacg accaggttcg tttcgaggtc   2924
ggcttcatgg acaccgatcc aaacctggag atcattgcac ctgctcgtga cttcgcatgg   2984
acccgcgaca aggctatcgc cttcgccgag gagaacaacg ttccaatcga gcagtccgtg   3044
aagtccccat ctccatcga ccagaacgtc tggggccgcg ctattgagac cggttacctg   3104
gaagatctgt ggaatgctcc aaccaaggac atctacgcat acaccgagga tccagctctg   3164
ggtaacgctc cagatgaggt catcatctcc ttcgagggtg gcaagccagt ctccatcgat   3224
ggccgtccag tctccgtact gcaggctatt gaagagctga accgtcgtgc aggcgcacag   3284
ggcgttggcc gccttgacat ggttgaggac cgtctcgtgg gcatcaagtc ccgcgaaatc   3344
tacgaagcac caggcgcaat cgcactgatt aaggctcacg aggctttgga agatgtcacc   3404
atcgagcgcg aactggctcg ctacaagcgt ggcgttgacg cacgttgggc tgaggaagta   3464
tacgacggcc tgtggttcgg acctctgaag cgctccctgg acgcgttcat tgattccacc   3524
caggagcacg tcaccggcga tatccgcatg gttctgcacg caggttccat caccatcaat   3584
ggtcgtcgtt ccagccactc cctgtacgac ttcaacctgg ctacctacga caccggcgac   3644
accttcgacc agaccctggc taagggcttt gtccagctgc acggtctgtc ctccaagatc   3704
gctaacaagc gcgatcgcga agctggcaac aactaagcca ccttttcaag catccagact   3764
agaacttcaa gtatttagaa agtagaagaa caccacatgg aacagcacgg aaccaatgaa   3824
ggtgcgctgt ggggcggccg cttctccggt ggaccctccg aggccatgtt cgccttgagt   3884
gtctccactc atttcgactg ggttttggcc ccttatgatg tgttggcctc caaggcacac   3944
gccaaggttt tgcaccaagc agagctactt tctgatgaag atctagccac catgctggct   4004
ggtcttgatc agctgggcaa ggatgtcgcc gacggaacct tcggtccgct gccttctgat   4064
gaggatgtgc acggcgcgat ggaacgcggt ctgattgacc gcgttggtcc tgaggtgggc   4124
ggccgtctgc gcgctggtcg ttcccgcaac gaccaggtgg caaccctgtt ccgcatgtgg   4184
gtccgcgacg cagtgcgcga catcgcgctg ggaacaaccg agcttgtcga c            4235
```

<210> SEQ ID NO 17
<211> LENGTH: 171
<212> TYPE: PRT
<213> ORGANISM: Brevibacterium flavum

<400> SEQUENCE: 17

```
Met Ser Leu Gly Ser Thr Pro Ser Thr Pro Glu Asn Leu Asn Pro Val
1               5                   10                  15

Thr Arg Thr Ala Arg Gln Ala Leu Ile Leu Gln Ile Leu Asp Lys Gln
            20                  25                  30

Lys Val Thr Ser Gln Val Gln Leu Ser Glu Leu Leu Asp Glu Gly
        35                  40                  45

Ile Asp Ile Thr Gln Ala Thr Leu Ser Arg Asp Leu Asp Glu Leu Gly
    50                  55                  60

Ala Arg Lys Val Arg Pro Asp Gly Gly Arg Ala Tyr Tyr Ala Val Gly
65                  70                  75                  80
```

```
Pro Val Asp Ser Ile Ala Arg Glu Asp Leu Arg Gly Pro Ser Glu Lys
             85                  90                  95

Leu Arg Arg Met Leu Asp Glu Leu Leu Val Ser Thr Asp His Ser Gly
           100                 105                 110

Asn Ile Ala Met Leu Arg Thr Pro Pro Gly Ala Ala Gln Tyr Leu Ala
           115                 120                 125

Ser Phe Ile Asp Arg Val Gly Leu Lys Glu Val Val Gly Thr Ile Ala
       130                 135                 140

Gly Asp Asp Thr Val Phe Val Leu Ala Arg Asp Pro Leu Thr Gly Lys
145                 150                 155                 160

Glu Leu Gly Glu Leu Leu Ser Gly Arg Thr Thr
                165                 170
```

<210> SEQ ID NO 18
<211> LENGTH: 25
<212> TYPE: DNA
<213> ORGANISM: Artificial Sequence
<220> FEATURE:
<223> OTHER INFORMATION: Synthetic DNA

<400> SEQUENCE: 18
cccgggtttt cttctgcaac tcggg                                       25

<210> SEQ ID NO 19
<211> LENGTH: 25
<212> TYPE: DNA
<213> ORGANISM: Artificial Sequence
<220> FEATURE:
<223> OTHER INFORMATION: Synthetic DNA

<400> SEQUENCE: 19
gtcgacaagc tcggttgttc ccagc                                       25

<210> SEQ ID NO 20
<211> LENGTH: 24
<212> TYPE: DNA
<213> ORGANISM: Artificial Sequence
<220> FEATURE:
<223> OTHER INFORMATION: Synthetic DNA

<400> SEQUENCE: 20
cccctagttc aaggcttgtt aatc                                        24

<210> SEQ ID NO 21
<211> LENGTH: 25
<212> TYPE: DNA
<213> ORGANISM: Artificial Sequence
<220> FEATURE:
<223> OTHER INFORMATION: Synthetic DNA

<400> SEQUENCE: 21
gtcttacctc ggctggttgg ccagc                                       25

<210> SEQ ID NO 22
<211> LENGTH: 23
<212> TYPE: DNA
<213> ORGANISM: Artificial Sequence
<220> FEATURE:
<223> OTHER INFORMATION: Synthetic DNA

<400> SEQUENCE: 22
tggttaacgg gatttcagca agg                                         23

-continued

<210> SEQ ID NO 23
<211> LENGTH: 23
<212> TYPE: DNA
<213> ORGANISM: Artificial Sequence
<220> FEATURE:
<223> OTHER INFORMATION: Synthetic DNA

<400> SEQUENCE: 23
gagcagctgg acaacagcct tga        23

<210> SEQ ID NO 24
<211> LENGTH: 2374
<212> TYPE: DNA
<213> ORGANISM: Corynebacterium glutamicum
<220> FEATURE:
<221> NAME/KEY: CDS
<222> LOCATION: (1025)..(1723)
<223> OTHER INFORMATION:

<400> SEQUENCE: 24

```
ccatttgctg aaggtgttac tctgcctggc ccaattcctg cgggcgaaga agtgaaaaac        60
cctgaacctt ttcagaagta actaaggccg caatccctcg attgctgcat caacgacggc       120
gtctgtgagt ctagctagag atctagattc caggcgccat cgttgccaat acatcggtgt       180
gtcaatgggt atctcatcga ggaggatcac ttctcctgct tttagcatgg gagcagcttg       240
ggtttcggga agaagtcccc aaccaaggcc tcggcgaatt gcctcaccaa aaccttccgc       300
cgacgggaca atggatacgc gcctgcgccc cacaggacca tcgacgcgcc cgtccaggtc       360
acggtcttga agcacatctt tgggaccgaa gcgtaagacg ggcatcgcag cccaatctag       420
tttcccatca accatgtagg catcccgcaa tgaggggtt gcaatggcca agtggcgcat        480
ggttccaagt tctactactt cacatcccgc acgggatta gcttcacggg ttaccgctcc        540 taaacatct ccacgccgca gcaaggataa tgtgtgcgct tcatcttcca gcgcagcgt         600 gagcgttgct ccaccccaag aagctacctc gttgaacacg ggaggaaacc atgtggatag       660
cgaatctgcg ttgatggcga tggttaacgg gatttcagca aggcgtccag atagttgcgc       720 tttagttct gcttgcagca acaccatttt ccgcgctgct tgcacaagga cttcacccgc        780
ttcggttgct ttggccggtt gggtgcgcga taccaacact cgacccacgt gatgctcgag       840
agctttaacg cgctgactca ccgccgaggg ggaaatggaa agggctaagg aggcgccttc       900
gaagctgcct tcatcaatga ttgagagcaa agtgtccagt tgaatggggt tcatgaagct       960
atattaaacc atgttaagaa ccaatcattt tacttaagta cttccatagg tcacgatggt      1020
```

| | | |
|---|---|---|
| gatc atg gaa atc ttc att aca ggt ctg ctt ttg ggg gcc agt ctt tta | 1069 | |
|      Met Glu Ile Phe Ile Thr Gly Leu Leu Leu Gly Ala Ser Leu Leu | | |
|       1          5           10           15 | | |

```
ctg tcc atc gga ccg cag aat gta ctg gtg att aaa caa gga att aag      1117
Leu Ser Ile Gly Pro Gln Asn Val Leu Val Ile Lys Gln Gly Ile Lys
             20                  25                  30 cgc gaa gga ctc att gcg gtt ctt ctc gtg tgt tta att tct gac gtc      1165
Arg Glu Gly Leu Ile Ala Val Leu Leu Val Cys Leu Ile Ser Asp Val
         35                  40                  45 ttt ttg ttc atc gcc ggc acc ttg ggc gtt gat ctt ttg tcc aat gcc      1213
Phe Leu Phe Ile Ala Gly Thr Leu Gly Val Asp Leu Leu Ser Asn Ala
     50                  55                  60 gcg ccg atc gtg ctc gat att atg cgc tgg ggt ggc atc gct tac ctg      1261
Ala Pro Ile Val Leu Asp Ile Met Arg Trp Gly Gly Ile Ala Tyr Leu
 65                  70                  75                  80 tta tgg ttt gcc gtc atg gca gcg aaa gac gcc atg aca aac aag gtg      1309
Leu Trp Phe Ala Val Met Ala Ala Lys Asp Ala Met Thr Asn Lys Val
```

```
                80                  85                  90                  95
gaa gcg cca cag atc att gaa gaa aca gaa cca acc gtg ccc gat gac      1357
Glu Ala Pro Gln Ile Ile Glu Glu Thr Glu Pro Thr Val Pro Asp Asp
                100                 105                 110 acg cct ttg ggc ggt tcg gcg gtg gcc act gac acg cgc aac cgg gtg      1405
Thr Pro Leu Gly Gly Ser Ala Val Ala Thr Asp Thr Arg Asn Arg Val
            115                 120                 125 cgg gtg gag gtg agc gtc gat aag cag cgg gtt tgg gta aag ccc atg      1453
Arg Val Glu Val Ser Val Asp Lys Gln Arg Val Trp Val Lys Pro Met
        130                 135                 140 ttg atg gca atc gtg ctg acc tgg ttg aac ccg aat gcg tat ttg gac      1501
Leu Met Ala Ile Val Leu Thr Trp Leu Asn Pro Asn Ala Tyr Leu Asp
    145                 150                 155 gcg ttt gtg ttt atc ggc ggc gtc ggc gcg caa tac ggc gac acc gga      1549
Ala Phe Val Phe Ile Gly Gly Val Gly Ala Gln Tyr Gly Asp Thr Gly
160                 165                 170                 175 cgg tgg att ttc gcc gct ggc gcg ttc gcg gca agc ctg atc tgg ttc      1597
Arg Trp Ile Phe Ala Ala Gly Ala Phe Ala Ala Ser Leu Ile Trp Phe
                180                 185                 190 ccg ctg gtg ggt ttc ggc gca gca gca ttg tca cgc ccg ctg tcc agc      1645
Pro Leu Val Gly Phe Gly Ala Ala Ala Leu Ser Arg Pro Leu Ser Ser
            195                 200                 205 ccc aag gtg tgg cgc tgg atc aac gtc gtc gtg gca gtt gtg atg acc      1693
Pro Lys Val Trp Arg Trp Ile Asn Val Val Val Ala Val Val Met Thr
        210                 215                 220 gca ttg gcc atc aaa ctg atg ttg atg ggt tagttttcgc gggttttgga        1743
Ala Leu Ala Ile Lys Leu Met Leu Met Gly
    225                 230 atcggtggcc ttcgcccaaa tgttgatgcc ggcgtcgtgg aaatctcat cgatcgcctc      1803 caactcggcg tcagaaaact ccaagttgtt gagtgaatca aggctgttgt ccagctgctc     1863
aactgacgaa gcaccaatca atgcactggt cacggtatcc gcgccgtact ctccttgctc     1923
gcgcagcacc catgcaagcg ccatctgcgc aagtgactgc ccgcgttcct gggcgatgtc     1983
attgagcttg cggaccatat caatattgtt cacgttcaac atgccctcag acagggactt     2043
accctggctg gcgcgggaac cctctggaat tccatcgaga tatttgtccg tgagcaggcc     2103
ctgcgcaagt ggtgagaaag caatgacgcc aagaccattg ttggcagctg actgcaacaa     2163
gttctcaccg tcatcgcccg gttcctccac ccaacgatta atgatggaat agcttggctg     2223
atgaatcaga gcgggcagc cctcctccgc catgaactca gccgcctccg ctgtgagctc      2283
tggaccgtag gaagaaatac ccacgtaaag agcctttcca gacgcaacaa tgtcacgcaa     2343
tgcgtacatg gtttcttcca aaggagtatc t                                    2374

<210> SEQ ID NO 25
<211> LENGTH: 233
<212> TYPE: PRT
<213> ORGANISM: Corynebacterium glutamicum

<400> SEQUENCE: 25

Met Glu Ile Phe Ile Thr Gly Leu Leu Leu Gly Ala Ser Leu Leu Leu
1               5                   10                  15

Ser Ile Gly Pro Gln Asn Val Leu Val Ile Lys Gln Gly Ile Lys Arg
            20                  25                  30

Glu Gly Leu Ile Ala Val Leu Leu Val Cys Leu Ile Ser Asp Val Phe
        35                  40                  45

Leu Phe Ile Ala Gly Thr Leu Gly Val Asp Leu Leu Ser Asn Ala Ala
    50                  55                  60
```

```
Pro Ile Val Leu Asp Ile Met Arg Trp Gly Ile Ala Tyr Leu Leu
65                  70                  75                  80

Trp Phe Ala Val Met Ala Ala Lys Asp Ala Met Thr Asn Lys Val Glu
                85                  90                  95

Ala Pro Gln Ile Ile Glu Glu Thr Glu Pro Thr Val Pro Asp Asp Thr
            100                 105                 110

Pro Leu Gly Gly Ser Ala Val Ala Thr Asp Thr Arg Asn Arg Val Arg
            115                 120                 125

Val Glu Val Ser Val Asp Lys Gln Arg Val Trp Val Lys Pro Met Leu
        130                 135                 140

Met Ala Ile Val Leu Thr Trp Leu Asn Pro Asn Ala Tyr Leu Asp Ala
145                 150                 155                 160

Phe Val Phe Ile Gly Gly Val Gly Ala Gln Tyr Gly Asp Thr Gly Arg
                165                 170                 175

Trp Ile Phe Ala Ala Gly Ala Phe Ala Ala Ser Leu Ile Trp Phe Pro
            180                 185                 190

Leu Val Gly Phe Gly Ala Ala Leu Ser Arg Pro Leu Ser Ser Pro
        195                 200                 205

Lys Val Trp Arg Trp Ile Asn Val Val Val Ala Val Val Met Thr Ala
    210                 215                 220

Leu Ala Ile Lys Leu Met Leu Met Gly
225                 230
```

<210> SEQ ID NO 26
<211> LENGTH: 30
<212> TYPE: DNA
<213> ORGANISM: Artificial Sequence
<220> FEATURE:
<223> OTHER INFORMATION: Synthetic DNA

<400> SEQUENCE: 26
gcgcggtacc agctccagtt caggaagcac                                    30

<210> SEQ ID NO 27
<211> LENGTH: 30
<212> TYPE: DNA
<213> ORGANISM: Artificial Sequence
<220> FEATURE:
<223> OTHER INFORMATION: Synthetic DNA

<400> SEQUENCE: 27
gcgctctaga aaatggcctg tgcaactccc                                    30

<210> SEQ ID NO 28
<211> LENGTH: 24
<212> TYPE: DNA
<213> ORGANISM: Artificial Sequence
<220> FEATURE:
<223> OTHER INFORMATION: Synthetic DNA

<400> SEQUENCE: 28
gtcttacctc ggctggtggg ccag                                          24

<210> SEQ ID NO 29
<211> LENGTH: 24
<212> TYPE: DNA
<213> ORGANISM: Artificial Sequence
<220> FEATURE:
<223> OTHER INFORMATION: Synthetic DNA

<400> SEQUENCE: 29 ccccctagttc aaggcttgtt aatc                                              24

<210> SEQ ID NO 30
<211> LENGTH: 39
<212> TYPE: DNA
<213> ORGANISM: Artificial Sequence
<220> FEATURE:
<223> OTHER INFORMATION: Synthetic DNA

<400> SEQUENCE: 30
agggaattcc ccgttctgga taatgttttt tgcgccgac                               39

<210> SEQ ID NO 31
<211> LENGTH: 58
<212> TYPE: DNA
<213> ORGANISM: Artificial Sequence
<220> FEATURE:
<223> OTHER INFORMATION: Synthetic DNA

<400> SEQUENCE: 31
cggatgcatc tagagttaac ctgcagggtg aaattgttat ccgctcacaa ttccacac          58

<210> SEQ ID NO 32
<211> LENGTH: 64
<212> TYPE: DNA
<213> ORGANISM: Artificial Sequence
<220> FEATURE:
<223> OTHER INFORMATION: Synthetic DNA

<400> SEQUENCE: 32
catttcctgc aggcaaagga gatgagcgta atggtgatca tggaaatctt cattacaggt        60
ctgc                                                                    64

<210> SEQ ID NO 33
<211> LENGTH: 50
<212> TYPE: DNA
<213> ORGANISM: Artificial Sequence
<220> FEATURE:
<223> OTHER INFORMATION: Synthetic DNA

<400> SEQUENCE: 33
gggcgagcta gaaagagctcc aaaacccgcg aaaactaacc catcaacatc                  50

<210> SEQ ID NO 34
<211> LENGTH: 21
<212> TYPE: DNA
<213> ORGANISM: Artificial Sequence
<220> FEATURE:
<223> OTHER INFORMATION: Synthetic DNA

<400> SEQUENCE: 34
acttctcccg cgagccagtt c                                                  21

<210> SEQ ID NO 35
<211> LENGTH: 21
<212> TYPE: DNA
<213> ORGANISM: Artificial Sequence
<220> FEATURE:
<223> OTHER INFORMATION: Synthetic DNA

<400> SEQUENCE: 35
ggcaagctta gcgcctctgt t                                                  21

METHOD FOR PRODUCING L-ARGININE

FIELD OF THE INVENTION

The present invention relates to a microorganism having an ability to produce L-arginine and a method for producing L-arginine using such a microorganism. L-arginine is an industrially useful amino acid as an ingredient of liver function promoting agents, amino acid infusions, comprehensive amino acid pharmaceuticals and so forth.

DESCRIPTION OF THE RELATED ART

Conventional L-arginine production by fermentation has been performed by utilizing wild-type strains of coryneform bacteria; coryneform bacteria resistant to certain agents including sulfa drugs, 2-thiazolealanine, α-amino-β-hydroxyvaleric acid and so forth; coryneform bacteria exhibiting auxotrophy for L-histidine, L-proline, L-threonine, L-isoleucine, L-methionine or L-tryptophan in addition to the resistance to 2-thiazolealanine (Japanese Patent Laid-open (Kokai) No. 54-44096); coryneform bacteria resistant to ketomalonic acid, fluoromalonic acid or monofluoroacetic acid (Japanese Patent Laid-open No. 57-18989); coryneform bacteria resistant to argininol (Japanese Patent Laid-open No. 62-24075); coryneform bacteria resistant to X-guanidine (X represents a derivative of fatty acid or aliphatic chain, Japanese Patent Laid-open No. 2-186995) and so forth.

On the other hand, there have been disclosed various techniques for increasing L-arginine producing ability by enhancing biosynthesis enzymes for L-arginine utilizing recombinant DNA techniques. For example, there have been disclosed methods for producing L-arginine by utilizing a microorganism belonging to the genus *Corynebacterium* or *Brevibacterium* which is made to harbor a recombinant DNA comprising a vector DNA and a DNA fragment containing genes for acetylornithine deacetylase, N-acetylglutamic acid-γ-semialdehyde dehydrogenase, N-acetyl glutamokinase, and argininosuccinase derived from a microorganism belonging to the genus *Escherichia* (Japanese Patent Publication (Kokoku) No. 5-23750), a microorganism such as a coryneform bacterium of which glutamate dehydrogenase activity is enhanced (EP 1057 893 A1), *Escherichia coli* introduced with N-acetylglutamate synthetase gene (argA) (refer to Japanese Patent Laid-open No. 57-5693) and so forth.

Further, as for coryneform bacteria, it has been elucidated that production of some enzymes of the L-arginine biosynthetic pathway is inhibited by L-arginine. Furthermore, it was reported that, while some of enzymes of L-arginine biosynthetic pathway were suppressed by L-arginine, the suppression of these enzymes by L-arginine was desensitized in mutant strains of *coryneform* bacteria showing improved L-arginine accumulation amounts (Agric. Biol. Chem., 43(1), 105, 1979).

Further, as for *Escherichia coli*, a repressor of L-arginine biosynthetic pathway and a gene coding for the repressor were identified (Proc. Natl. Acad. Sci. U.S.A. (1987), 84(19), 6697-701), and binding interactions of the repressor protein and genes of various L-arginine biosynthetic pathway were also investigated (Proc. Natl. Acad. Sci. U.S.A. (1987), 84(19), 6697-701, J. Mol. Biol. (1992), 226, 367-386).

However, any repressor proteins of the L-arginine biosynthetic pathway have not been identified in *coryneform* bacteria. While a nucleotide sequence of the repressor protein gene (argR) and an amino acid sequence assumed to be encoded thereby are registered in a gene database, GenBank (AF049897), the gene is considered to be designated argR because of the homology between the aforementioned amino acid sequence and known arginine repressors.

Meanwhile, a protein having a function of specifically excreting an L-amino acid to the outside of a cell of microorganism and a gene therefor have recently been identified, and in particular, Vrlijc et al. identified a gene involved in the extracellular excretion of L-lysine from *Corynebacterium* bacteria (Vrlijc M., Sahm H., Eggeling L., Molecular Microbiology, 22:815-826 (1996)). This gene was designated as lysE, and it was reported that L-lysine producing ability of a *Corynebacterium* bacterium was improved by enhancing this gene in the *Corynebacterium* bacterium (WO97/23597). Further, it is also known that productivities of some L-amino acids can be improved by increasing expression amounts of amino acid excreting proteins in *Escherichia coli* (Japanese Patent Laid-open No. 2000-189180). For example, it has been reported that productivities of lysine and arginine were improved by introducing multiple copies of yggA gene into *Escherichia coli* (Japanese Patent Laid-open Publication No. 2000-189180). Further, it has also been reported that productivities of cystine, cysteine and so forth were improved by enhancing expression of ORF306 gene in *Escherichia coli* (EP885962). However, it has not known that the lysE gene has a function of excreting an amino acid other than L-lysine.

SUMMARY OF THE INVENTION

An object of the present invention is to improve L-arginine producing ability of a microorganism such as *coryneform* bacteria and bacteria belonging to the genus *Escherichia* and thereby provide a method for efficiently producing L-arginine.

In the course of the study about L-arginine producing bacteria, the inventors of the present invention found that L-arginine producing ability could be improved by enhancing expression of the lysE gene. Furthermore, they also found that the L-arginine producing ability could be markedly improved by combining enhancement of lysE and disruption of the argR gene or enhancement of activity of an enzyme in the L-arginine biosynthetic pathway, and thus accomplished the present invention. That is, the present invention provides the followings.

(1) A microorganism which has L-arginine producing ability and has been modified so that expression of lysE gene should be enhanced.

(2) The microorganism according to (1), wherein the expression of lysE gene is enhanced by increasing copy number of the lysE gene or modifying an expression regulatory sequence of the lysE gene so that the intracellular expression of the lysE gene in the microorganism should be enhanced.

(3) The microorganism according to (1) or (2), which has been further modified so that an arginine repressor should not function normally.

(4) The microorganism according to (3), wherein the arginine repressor does not function normally due to disruption of a gene coding for the arginine repressor on a chromosome.

(5) The microorganism according to any one of (1) to (4), which has been further modified so that intracellular activity of an enzyme in L-arginine biosynthetic pathway should be enhanced.

(6) The microorganism according to any one of (1) to (5), wherein the microorganism is a *coryneform* bacterium.
(7) The microorganism according to any one of (1) to (5), wherein the microorganism is a bacterium belonging to the genus *Escherichia*.
(8) A method for producing L-arginine, which comprises culturing the microorganism according to any one of (1) to (7) in a medium to produce and accumulate L-arginine in the medium and collecting the L-arginine from the medium.

In the present invention, "L-arginine producing ability (ability to produce L-arginine)" means an ability of the microorganism of the present invention to accumulate L-arginine in a medium when the microorganism is cultured in the medium. This L-arginine producing ability may be possessed by the microorganism as a property of the microorganism as a wild strain, or a property imparted or enhanced by breeding.

According to the present invention, L-arginine producing ability of microorganisms such as *coryneform* bacteria and bacterium belonging to the genus *Escherichia* having L-arginine producing ability can be improved.

DETAILED EXPLANATION OF THE INVENTION

Figure 1:
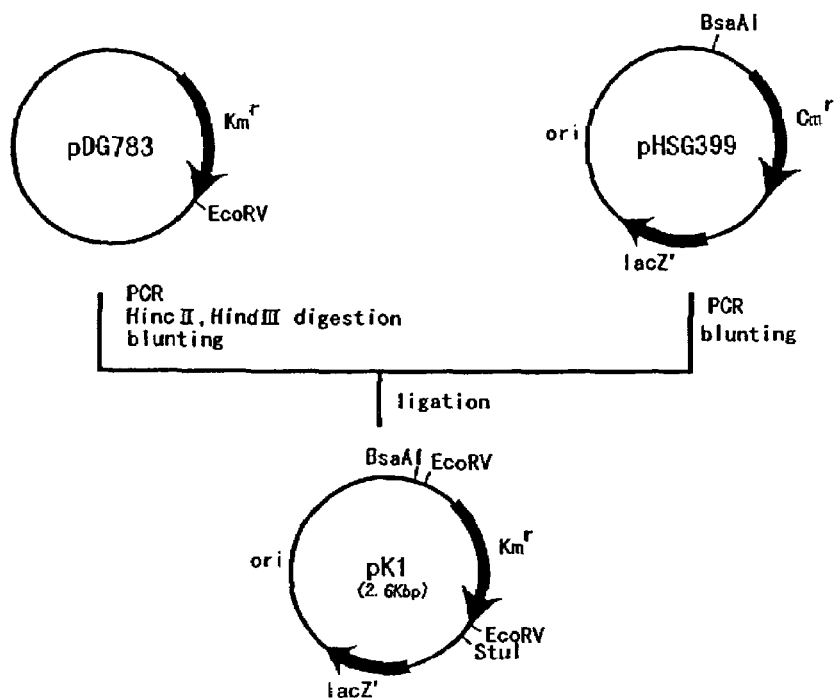
FIG. 1 shows construction process of plasmid pK1.

Hereafter, the present invention will be explained in detail.

<1> Microorganism of the Present Invention

The microorganism of the present invention is a microorganism which has L-arginine producing ability and has been modified so that expression of the lysE gene should be enhanced. The microorganism of the present invention may be one obtained by enhancing expression of the lysE gene of a microorganism having L-arginine producing ability or one obtained by enhancing expression of the lysE gene of a microorganism and then imparting L-arginine producing ability to the microorganism.

Specific examples of the microorganism of the present invention include microorganism having lysE gene or lysE gene homologue, concretely, *coryneform* bacteria, bacteria belonging to the genus *Bacillus, Serratia* or *Escherichia*, yeasts belonging to the genus *Saccharomyces* or *Candida*. Of these, *coryneform* bacteria and a bacterium belonging to the genus *Escherichia* are preferred.

Exemplary microorganisms include *Bacillus subtilis* as bacteria belonging to the genus *Bacillus, Serratia marcescens* as bacteria belonging to the genus *Serratia, Escherichia coli* as bacteria belonging to the genus *Escherichia*, *Saccharomyces cerevisiae* as yeasts belonging to the genus *Saccharomyces, Candida tropicalis* as yeasts belonging to the genus *Candida*.

Exemplary microorganisms having L-arginine producing ability include *Bacillus subtilis* resistant to 5-azauracil, 6-azauracil, 2-thiouracil, 5-fluorouracil, 5-bromouracil, 5-azacytosine, 6-azacytosine and so forth, *Bacillus subtilis* resistant to arginine hydroxamate and 2-thiouracil, *Bacillus subtilis* resistant to arginine hydroxamate and 6-azauracil (refer to Japanese Patent Laid-open No. 49-1268191),

*Bacillus subtilis* resistant to histidine analogues or tryptophan analogues (refer to Japanese Patent Laid-open No. 52-114092), a mutant strain of *Bacillus subtilis* exhibiting auxotrophy for at least one of methionine, histidine, threonine, proline, isoleucine, lysine, adenine, guanine and uracil (or uracil precursor) (refer to Japanese Patent Laid-open No. 52-99289),

*Bacillus subtilis* resistant to arginine hydroxamate (refer to Japanese Patent Publication No. 51-6754),

*Serratia marcescens* exhibiting succinic acid auxotrophy or resistance to nucleic acid base analogues (Japanese Patent Laid-open No. 58-9692),

*Serratia marcescens* deficient in ability to metabolize arginine and exhibiting resistance to arginine antagonists and canavanine and auxotorophy for lysine (refer to Japanese Patent Laid-open No. 52-8729),

*Escherichia coli* introduced with the argA gene (refer to Japanese Patent Laid-open No. 57-5693),

*Saccharomyces cerevisiae* resistant to arginine, arginine hydroxamate, homoarginine, D-arginine and canavanine, or resistant to arginine hydroxamate and 6-azauracil (refer to Japanese Patent Laid-open No. 53-143288),

*Candida tropicalis* resistant to canavanine (refer to Japanese Patent Laid-open No. 53-3586) and so forth.

*Coryneform* bacteria include those bacteria having been hitherto classified into the genus *Brevibacterium* but united into the genus *Corynebacterium* at present (Int. J. Syst. Bacteriol., 41, 255 (1981)), and include bacteria belonging to the genus *Brevibacterium* closely relative to the genus *Corynebacterium*. Examples of such *coryneform* bacteria are listed below.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium album*
*Brevibacterium cerinum*
*Microbacterium ammoniaphilum*

The *coryneform* bacteria that have the L-arginine producing ability are not particularly limited so long as they have the L-arginine producing ability. They include, for example, wild-type strains of *coryneform* bacteria; *coryneform* bacteria resistant to certain agents including sulfa drugs, 2-thiazolealanine, α-amino-β-hydroxyvaleric acid and so forth; *coryneform* bacteria exhibiting auxotrophy for L-histidine, L-proline, L-threonine, L-isoleucine, L-methionine or L-tryptophan in addition to resistance to 2-thiazolealanine (Japanese Patent Laid-open No. 54-44096); *coryneform* bacteria resistant to ketomalonic acid, fluoromalonic acid or monofluoroacetic acid (Japanese Patent Laid-open No. 57-18989); *coryneform* bacteria resistant to argininol (Japanese Patent Laid-open No. 62-24075); *coryneform* bacteria resistant to X-guanidine (X represents a derivative of fatty acid or aliphatic chain, Japanese Patent Laid-open No. 2-186995) and so forth.

Specifically, the following bacterial strains can be exemplified.

*Brevibacterium flavum* AJ11169 (FERM P-4161)

*Brevibacterium lactofermentum* AJ12092 (FERM P-7273)

*Brevibacterium flavum* AJ11336 (FERM P-4939)

*Brevibacterium flavum* AJ11345 (FERM P-4948)

*Brevibacterium lactofermentum* AJ12430 (FERM BP-2228)

AJ11169 was deposited on Aug. 3, 1977 at the independent administrative corporation, National Institute of Advanced Industrial Science and Technology, International Patent Organism Depositary (Chuo Dai-6, 1-1 Higashi 1-Chome, Tsukuba-shi, Ibaraki-ken, Japan, postal code: 305-5466)(formerly, the Fermentation Research Institute, Agency of Industrial Science and Technology, the same shall apply to the same occasions hereafter) and given an accession number of FERM P-4161. Then, it was converted to an international deposit based on the Budapest Treaty on Sep. 27, 1999 and given an accession number of FERM BP-6892.

AJ12092 was deposited on Sep. 29, 1983 at the independent administrative corporation, National Institute of Advanced Industrial Science and Technology, International Patent Organism Depositary and given an accession number of FERM P-7273. Then, it was converted to an international deposit based on the Budapest Treaty on Oct. 1, 1999 and given an accession number of FERM BP-6906.

AJ11336 was deposited on Apr. 25, 1979 at the independent administrative corporation, National Institute of Advanced Industrial Science and Technology, International Patent Organism Depositary and given an accession number of FERM P-4939. Then, it was converted to an international deposit based on the Budapest Treaty on Sep. 27, 1999 and given an accession number of FERM BP-6893.

AJ11345 was deposited on Apr. 25, 1979 at the independent administrative corporation, National Institute of Advanced Industrial Science and Technology, International Patent Organism Depositary and given an accession number of FERM P-4948. Then, it was converted to an international deposit based on the Budapest Treaty on Sep. 27, 1999 and given an accession number of FERM BP-6894.

AJ12430 was deposited on Dec. 26, 1988 at the independent administrative corporation, National Institute of Advanced Industrial Science and Technology, International Patent Organism Depositary as an international deposit based on the Budapest Treaty, and given an accession number of FERM BP-2228.

As the bacterium belonging to the genus *Escherichia*, those mentioned in the work of Neidhardt et al. (Neidhardt, F. C. et al., *Escherichia coli* and *Salmonella Typhimurium*, American Society for Microbiology, Washington D.C., 1208, Table 1) such as *Escherichia coli* can be utilized.

As bacterium belonging to the genus *Escherichia* having L-arginine producing ability, the *Escherichia coli* 237 strain (Russian Patent Application No. 2000117677) and so forth can be mentioned.

The first aspect of the microorganism of the present invention is a bacterium having L-arginine producing ability such as those mentioned above, which is modified so that expression of the lysE gene should be enhanced.

The second aspect of the microorganism of the present invention is such a microorganism as mentioned above, which has been further modified so that an arginine repressor should not function normally.

The third aspect of the microorganism of the present invention is a microorganism of the aforementioned first or second aspect of the present invention, which has been further modified so that intracellular activity of an enzyme in L-arginine biosynthetic pathway should be enhanced.

Hereafter, each embodiment will be explained.

(1) Microorganism of Which Expression of lysE Gene is Enhanced

Enhancement of the expression of the lysE gene of a microorganism can be attained by introducing a mutation into a gene coding for a protein involved in an L-lysine excretion system so that activity of the protein should be increased, or by using a genetic recombination technique utilizing the gene. Specifically, the gene may be the lysE gene (Vrlijc M., Sahm H., Eggeling L., Molecular Microbiology 22:815-826 (1996), WO97/23597).

Hereafter, explanation will be made by referring to the lysE gene as an example.

Example of the mutation that increases the activity of the protein encoded by the lysE gene (LysE protein) include a mutation of a promoter sequence that increases transcription amount of the lysE gene, a mutation in the coding region of the lysE gene that increases specific activity of the LysE protein and so forth.

Further, as for enhancement of the LysE activity by using a genetic recombination technique, it can be attained by, for example, increasing copy number of the lysE gene in a cell. For example, a recombinant DNA can be prepared by ligating a DNA fragment containing the lysE gene with a vector functioning in a microorganism, preferably a multi-copy type vector, and introduced into the microorganism to transform it.

As the lysE gene, a gene derived from any of *coryneform* bacteria and bacterium belonging to the genus *Escherichia*, or a gene derived from any of other organisms can be used. Among these, a gene derived from of a *coryneform* bacterium or bacterium belonging to the genus *Escherichia* is preferred in view of ease of expression.

Since the sequence of the lysE gene of *coryneform* bacteria has already been elucidated (GenBank Accession x96471), the lysE gene can be obtained by PCR (polymerase chain reaction, refer to White, T. J. et al., Trends Genet., 5, 185 (1989)) utilizing primers prepared based on the nucleotide sequence, for example, the primers shown in Sequence Listing as SEQ ID NOS: 23 and 24, and chromosomal DNA of *coryneform* bacterium as a template. A nucleotide sequence of a DNA fragment containing *Corynebacterium glutamicum* lysG and lysE genes (GenBank Accession x96471) is shown as SEQ ID NO: 25, and the amino acid sequence of LysE is shown as SEQ ID NO: 26. LysG is encoded by a complementary strand at a position corresponding to the nucleotide numbers 1723-2352 of SEQ ID NO: 25.

A lysE gene of any of other microorganisms can also be obtained from chromosomal DNA or a chromosomal DNA library of a microorganism by PCR utilizing oligonucleotides prepared based on a known lysE gene in the microorganism, a lysE gene of another microorganism or sequence information of the LysE protein as primers, or by the hybridization method utilizing an oligonucleotide prepared based on the aforementioned sequence information as a probe.

Further, the lysE gene used for the present invention is not limited to a wild type gene, and it may be a mutant or artificially modified gene coding for the protein including substitution, deletion, insertion or addition of one or several amino acid residues at one or more sites so long as the functions of the encoded LysE protein are not defected. Although the number of "several" amino acids referred to herein differs depending on position or type of amino acid residues in the three-dimensional structure of the protein, it may be specifically 2 to 30, preferably 2 to 20, more preferably 2 to 10. As a DNA coding for the substantially same protein as LysE as described above, there is exemplified a DNA that is hybridizable with a probe having a nucleotide sequence comprising, for example, the nucleotide sequence corresponding to nucleotide numbers of 1025 to 1723 of SEQ ID NO: 25, under the stringent conditions, and codes for a protein having the same or similar activity as LysE. The "stringent conditions" referred to herein is a condition under which so-called specific hybrid is formed, and non-specific hybrid is not formed. It is difficult to clearly express this condition by using any numerical value. However, for example, the stringent conditions are exemplified by a condition under which DNAs having high homology, for example, DNAs having homology of not less than 50% are hybridized with each other, but DNAs having homology lower than the above are not hybridized with each other. Alternatively, the stringent conditions are exemplified by a condition under which DNAs are hybridized with each other at a salt concentration corresponding to an ordinary condition of washing in Southern hybridization, i.e., 1×SSC, 0.1% SDS, preferably 0.1×SSC, 0.1% SDS, at 60° C.

The chromosomal DNA can be prepared from a bacterium serving as a DNA donor by, for example, the method of Saito and Miura (refer to H. Saito and K. Miura, Biochem. Biophys. Acta, 72, 619 (1963), Text for Bioengineering Experiments, Edited by the Society for Bioscience and Bioengineering, Japan, pp. 97-98, Baifukan, 1992) or the like.

If the lysE gene amplified by PCR is ligated to a vector DNA autonomously replicable in a cell of *Escherichia coli* and/or a *coryneform* bacterium to prepare a recombinant DNA and this is introduced into *Escherichia coli*, subsequent procedures become easy. Examples of the vector autonomously replicable in a cell of *Escherichia coli* include pUC19, pUC18, pHSG299, pHSG399, pHSG398, RSF1010, pBR322, pACYC184, pMW219 and so forth.

A vector that functions in a *coryneform* bacterium means, for example, a plasmid that can autonomously replicate in a *coryneform* bacterium. Specific examples thereof include the followings.

pAM330 (refer to Japanese Patent Laid-open Publication No. 58-67699)

pHM1519 (refer to Japanese Patent Laid-open Publication No. 58-77895)

pSFK6 (refer to Japanese Patent Laid-open Publication No. 2000-262288)

Moreover, if a DNA fragment having an ability to make a plasmid autonomously replicable in a *coryneform* bacterium is excided from these vectors and inserted into the aforementioned vectors for *Escherichia coli*, they can be used as a so-called shuttle vector autonomously replicable in both of *Escherichia coli* and *coryneform* bacterium.

Examples of such a shuttle vector include those mentioned below. There are also indicated microorganisms that harbor each vector, and accession numbers thereof at the international depositories are shown in the parentheses, respectively.

pAJ655 *Escherichia coli* AJ11882 (FERM BP-136)
  *Corynebacterium glutamicum* SR8201 (ATCC 39135)
pAJ1844 *Escherichia coli* AJ11883 (FERM BP-137)
  *Corynebacterium glutamicum* SR8202 (ATCC 39136)
pAJ611 *Escherichia coli* AJ11884 (FERM BP-138)
pAJ3148 *Corynebacterium glutamicum* SR8203 (ATCC 39137)
pAJ440 *Bacillus subtilis* AJ11901 (FERM BP-140)
pHC4 *Escherichia coli* AJ12617 (FERM BP-3532)

These vectors can be obtained from the deposited microorganisms as follows. That is, microbial cells collected in their exponential growth phase are lysed by using lysozyme and SDS, and centrifuged at 30000×g. The supernatant obtained from the lysate is added with polyethylene glycol, fractionated and purified by cesium chloride-ethidium bromide equilibrium density gradient centrifugation.

In order to prepare a recombinant DNA by ligating a lysE gene and a vector that can function in a cell of *coryneform* bacterium, a vector is digested with a restriction enzyme corresponding to the terminus of the lysE gene. Ligation is usually performed by using a ligase such as T4 DNA ligase.

To introduce the recombinant DNA prepared as described above into a microorganism, any known transformation methods that have hitherto been reported can be employed. For instance, employable are a method of treating recipient cells with calcium chloride so as to increase the permeability of the cells for DNA, which has been reported for *Escherichia coli* K-12 (Mandel, M. and Higa, A., J. Mol. Biol., 53, 159 (1970)), and a method of preparing competent cells from cells which are at the growth phase followed by introducing the DNA thereinto, which has been reported for *Bacillus subtilis* (Duncan, C. H., Wilson, G. A. and Young, F. E., Gene, 1, 153 (1977)). In addition to these, also employable is a method of making DNA-recipient cells into protoplasts or spheroplasts, which can easily take up recombinant DNA, followed by introducing the recombinant DNA into the DNA-acceptor cells, which is known to be applicable to *Bacillus subtilis*, actinomycetes and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)). The transformation of *coryneform* bacteria can also be performed by the electroporation method (Sugimoto et al., Japanese Patent Laid-open No. 2-207791).

Increase of copy number of lysE gene can also be achieved by introducing multiple copies of the lysE gene into chromosomal DNA of microorganism. In order to introduce multiple copies of the lysE gene into chromosomal DNA of microorganism, homologous recombination is carried out for sequences whose multiple copies exist in the chromosomal DNA as targets. As sequences whose multiple copies exist in the chromosomal DNA, repetitive DNA, inverted repeats existing at the end of a transposable element can be used. Also, as disclosed in Japanese Patent Laid-open No. 2-109985, it is possible to incorporate the lysE gene into transposons, and allow them to be transferred to introduce multiple copies of the gene into the chromosomal DNA.

Enhancement of the lysE activity can also be attained by, besides being based on the aforementioned gene amplification, replacing an expression regulatory sequence such as a promoter for the lysE gene on chromosomal DNA or plasmid, with a stronger one (WO00/18935). For example, lac promoter, trp promoter, trc promoter and so forth are known as strong promoters. Further, it is also possible to introduce nucleotide substitution or the like into the promoter region of lysE gene to modify it into a more potent promoter. The expression of the lysE gene is enhanced by such substitution or modification of the promoter. Such modifications of expression regulatory sequences may be combine with the increasing of the copy number of the lysE gene.

The substitution of expression regulatory sequence can also be attained, for example, in the same manner as the gene substitution using a temperature sensitive plasmid described later. Examples of the temperature sensitive plasmid for *coryneform* bacteria include p48K and pSFKT2 (refer to Japanese Patent Laid-open Publication No. 2000-262288 for these), pHSC4 (refer to France Patent Laid-open Publication No. 2667875, 1992 and Japanese Patent Laid-open Publication No. 5-7491) and so forth. These plasmids can autonomously replicate at least at a temperature of 25° C., but cannot autonomously replicate at a temperature of 37° C. in *coryneform* bacteria. Although pSFKT2 was used for the substitution for the promoter sequence of the GDH gene in the example mentioned later, the gene substitution can be performed in a similar manner by using pHSC4 instead of pSFKT2. *Escherichia coli* AJ12571 harboring pHSC4 was deposited on Oct. 11, 1990 at the independent administrative corporation, National Institute of Advanced Industrial Science and Technology, International Patent Organism Depositary (Chuo Dai-6, 1-1 Higashi 1-Chome, Tsukuba-shi, Ibaraki-ken, Japan, postal code: 305-5466) and given an accession number of FERM P-11763. Then, it was converted to an international deposit under the provisions of the Budapest Treaty on Aug. 26, 1991, and given an accession number of FERM BP-3524.

(2) Microorganism in Which Arginine Repressor does not Function Normally

In the present invention, the "arginine repressor" refers to a protein that has an effect of suppressing the L-arginine biosynthesis, and if expression amount of a gene that codes for this protein increases in a microorganism, L-arginine producing ability will be reduced, and if the expression amount decreases or the protein disappears, the L-arginine producing ability will be improved. Hereafter, a gene coding for the arginine repressor is also called argR gene.

The term "arginine repressor does not function normally" means that the activity of the arginine repressor is reduced or eliminated as compared with a wild type strain or unmodified strain.

A microorganism in which the arginine repressor does not function in a normal manner can be obtained by modifying its argR gene so that the activity of its gene product, the arginine repressor, should be reduced or eliminated, or the transcription of the argR gene should be reduced or eliminated. Such a microorganism can be obtained by, for example, replacing the chromosomal argR gene with an argR gene that does not function in a normal manner (occasionally referred to as "disrupted argR genes" hereinafter) through, for example, homologous recombination based on genetic recombination techniques (Experiments in Molecular Genetics, Cold Spring Harbor Laboratory Press (1972); Matsuyama, S. and Mizushima, S., J. Bacteriol., 162, 1196 (1985)).

When a plasmid carrying a sequence exhibiting homology with a chromosomal sequence or the like is introduced into a corresponding cell, recombination occurs at a site of the homologous sequence at a certain frequency, and thus the introduced plasmid as a whole is integrated into the chromosome. Then, by causing recombination again at the site of the homologous sequence in the chromosome, the plasmid may be eliminated again from the chromosome. However, depending on the position at which the recombination is caused, the disrupted gene may remain on the chromosome, while the original normal gene may be eliminated from the chromosome together with the plasmid. By selecting such strains, a strain in which the normal argR gene is replaced with the disrupted argR gene can be obtained.

Such a gene disruption technique based on the homologous recombination has already been established, and a method utilizing a linear DNA, method utilizing temperature sensitive plasmid or the like can be used therefor. The argR gene can also be disrupted by using a plasmid that contains the argR gene inserted with a marker gene such as drug resistance gene, and cannot replicate in a target cell of microorganism. That is, in a transformant that has been transformed with such a plasmid and hence acquired drug resistance, the marker gene is integrated in chromosome DNA. It is likely that this marker gene has been integrated by homologous recombination of the argR gene present at the both sides of the marker with the argR on the chromosome, and therefore a gene disrupted strain can efficiently be selected.

Specifically, a disrupted argR gene used for the gene disruption can be obtained by deletion of a certain region of argR gene by means of digestion with restriction exzyme(s) and religation; by insertion of another DNA fragment (marker gene etc.) into the argR gene, or by introducing substitution, deletion, insertion, addition or inversion of one or more nucleotides in a nucleotide sequence of coding region of argR gene, its promoter region or the like by means of site-specific mutagenesis (Kramer, W. and Frits, H. J., Methods in Enzymology, 154, 350 (1987)) or treatment with a chemical reagent such as sodium hyposulfite and hydroxylamine (Shortle, D. and Nathans, D., Proc. Natl. Acad. Sci. U.S.A., 75, 270(1978)) or the like, so that the activity of the encoded repressor should be reduced or eliminated, or transcription of the argR gene should be reduced or eliminated. Among these embodiments, a method utilizing deletion of a certain region of the argR gene by digestion with a restriction exzyme and religation, or insertion of another DNA fragment into the argR gene is preferred in view of reliability and stability.

A plasmid for the argR gene disruption can be produced by performing PCR (polymerase chain reaction) using a plasmid containing the argR gene and its flanking regions as a template and primers corresponding the terminal portions or franking regions of the argR gene to amplify a portion except for an internal portion or the whole portion of the argR gene, and cyclizing the obtained amplified product. In the examples mentioned later, the argR gene was disrupted by this method.

The argR gene can be obtained from chromosomal DNA of a microorganism by PCR using oligonucleotides prepared based on a known nucleotide sequence of the argR gene as primers. The argR gene can also be obtained from a chromosome DNA library of a microorganism by a hybridization technique using an oligonucleotide prepared based on a known nucleotide sequence of the argR gene as a probe. For the purpose of the present invention, because the argR gene is used for preparing a disrupted argR gene, it is not necessarily required to contain the full length, and it may contain a length required to cause gene disruption.

The origin of the argR gene is not particularly limited, so long as it has such a degree of homology that it should cause homologous recombination with the argR gene of a target microorganism. Specifically, the argR gene of the *Brevibacterium flavum,* which has the nucleotide sequence shown as SEQ ID NO: 17, and the argR gene of *Corynebacterium glutamicum* (GenBank accession AF049897) can be mentioned as the argR genes of *coryneform* bacteria. These argR genes are highly homologous, and it is considered that even an argR gene of *coryneform* bacterium of a genus or species different from that of a *coryneform* bacterium of which argR gene is to be disrupted may also be used for the gene disruption.

In the present invention, the amino acid sequence shown as SEQ ID NO: 18 or an amino acid sequence exhibiting homology to the amino acid sequence means an amino acid sequence that is encoded by an argG gene having such a degree of homology that it should cause homologous recombination with the argG gene coding to the amino acid sequence shown as SEQ ID NO: 18 (for example, an argG gene having the nucleotide sequence shown as SEQ ID NO: 17). The homology is, for example, preferably 70% or more, more preferably 80% or more, still more preferably 90% or more. As argG gene as described above, there is exemplified a DNA that is hybridizable with a probe having a nucleotide sequence comprising, for example, the nucleotide sequence corresponding to nucleotide numbers of 1852 to 2364 of SEQ ID NO: 17, under the stringent conditions. The "stringent conditions" referred to herein is a condition under which so-called specific hybrid is formed, and non-specific hybrid is not formed. It is difficult to clearly express this condition by using any numerical value. However, for example, the stringent conditions are exemplified by a condition under which DNAs having high homology, for example, DNAs having homology of not less than 50% are hybridized with each other, but DNAs having homology lower than the above are not hybridized with each other. Alternatively, the stringent conditions are exemplified by a condition under which DNAs are hybridized with each other at a salt concentration corresponding to an ordinary condition of washing in Southern hybridization, i.e., 1×SSC, 0.1% SDS, preferably 0.1×SSC, 0.1% SDS, at 60° C.

As the primers used for PCR, any primers that allow amplification of the argR gene can be used. Specific examples thereof include the oligonucleotides having the nucleotide sequences shown as SEQ ID NOS: 19 and 20.

Further, examples of the marker gene include drug resistance genes such as a kanamycin resistance gene. A kanamycin resistance gene can be obtained by PCR amplification from a known plasmid containing a kanamycin resistance gene of *Streptococcus faecalis,* for example, pDG783 (Anne-Marie Guerout-Fleury et al., Gene, 167, 335-337 (1995)).

When a drug resistance gene is used as the marker gene, an argR gene-disrupted strain can be obtained by inserting the drug resistance gene into a suitable site of the argR gene carried by a plasmid, transforming a microorganism with the plasmid, and selecting a drug resistant transformant. Disruption of argR gene on a chromosome can be confirmed by analyzing the argR gene or the marker gene on the chromosome by Southern blotting, PCR or the like. Integration of the kanamycin resistance gene into chromosomal DNA can be confirmed by PCR using primers that allow amplification of the kanamycin resistance gene (e.g., oligonucleotides having the nucleotide sequences shown as SEQ ID NOS: 1 and 2).

(3) Enhancement of Enzyme Activity of L-arginine Biosynthetic Pathway

Enhancement of enzyme activity of L-arginine biosynthetic pathway can be attained by introducing a mutation into a gene coding for the enzyme so that intracellular activity of an enzyme of the L-arginine biosynthetic pathway should be enhanced, or by using a genetic recombination technique utilizing the gene. The enzyme in L-arginine biosynthetic pathway may be one or more kinds of enzymes selected from N-acetylglutamyl phosphate reductase (argC), ornithine acetyltransferase (argJ), N-acetylglutamate kinase (argB), acetylornithine transaminase (argD), ornithine carbamoyltransferase (argF), argininosuccinate synthase (argG) and argininosucciniate lyase (argH). The designations of the genes coding for these enzymes are indicated in the parentheses after the name of the enzymes, respectively.

Further, the L-arginine producing ability can also be increased by enhancing glutamate dehydrogenase activity (EP 1057 893 A1).

Enhancement of enzyme activity of L-arginine biosynthetic pathway using a genetic recombination technique can be performed by increasing copy number of each gene or by modifying an expression regulatory sequence of those genes so that the expression of each gene should be enhanced, as in the enhancement of the LysE activity described above.

The nucleotide sequences of those genes of *Corynebacterium glutamicum* are registered at GenBank as Accession AF049897. In *Corynebacterium glutamicum,* these genes locate on chromosomal DNA in the order of argC, argJ, argB, argD, argF, argR, argG and argH, and they can be obtained by PCR using primers such as those shown as SEQ ID NOS: 27 and 28 and chromosomal DNA of *Corynebacterium glutamicum* or *Brevibacterium lactofermentum* as a template. Further, if normal argR is introduced into a *coryneform* bacterium together with another gene for an enzyme in L-arginine biosynthetic pathway, the enhancement of L-arginine productivity is inhibited. Therefore, in the present invention, it is preferable to disrupt or delete argR in the obtained PCR amplified fragment. This can be attained by, for example, performing PCR using a plasmid containing the PCR amplified fragment as a template and oligonucleotides having the nucleotide sequences shown as SEQ ID NOS: 29 and 30 as primers.

In the present invention, enhancement of an enzyme activity of L-arginine biosynthetic pathway may be combined with the disruption of the argR gene on a chromosome.

<2> Method for Producing L-arginine

L-arginine can be efficiently produced by culturing a microorganism showing enhanced expression of the lysE gene and having L-arginine producing ability obtained as described above in a medium to produce and accumulate L-arginine in culture, and collecting the L-arginine from the culture.

The medium to be used may be selected from well-known media conventionally used for fermentative production of amino acids utilizing microorganisms. That is, it may be a usual medium that contains a carbon source, nitrogen source, inorganic ions, and other organic ingredients as required.

As the carbon source, there can be used saccharides such as glucose, sucrose, lactose, galactose, fructose or starch hydrolysate, alcohols such as glycerol or sorbitol, or organic acids such as fumaric acid, citric acid or succinic acid.

As the nitrogen source, there can be used inorganic ammonium salts such as ammonium sulfate, ammonium chloride or ammonium phosphate, organic nitrogen such as soybean protein hydrolysate, ammonia gas, aqueous ammonia and so forth.

It is desirable to add required substances such as vitamin $B_1$, yeast extract and so forth to the medium in appropriate amounts as organic trace nutrients. Other than the above, potassium phosphate, magnesium sulfate, iron ion, manganese ion and so forth are added in small amounts as required.

The culture is preferably carried out under an aerobic condition for 1-7 days. The culture temperature is preferably controlled to be 24° C. to 37° C., and pH is preferably controlled to be 5-9 during the culture. Inorganic or organic, acidic or alkaline substances as well as ammonia gas and so forth can be used for pH adjustment. L-arginine can be collected from the fermentation broth usually by a combination of well-known techniques such as methods utilizing ion exchange resins and other techniques.

EXAMPLES

Hereafter, the present invention will be explained more specifically with reference to the following examples.

Example 1

Constructions of Shuttle Vector for *Escherichia coli* and *coryneform* Bacterium and Temperature Sensitive Vector First, a vector for introducing an argR gene into a *coryneform* bacterium and a temperature sensitive vector for producing an argR deficient strain of *coryneform* bacterium were constructed.

<1> Construction of Vector having Drug Resistance Gene of *Streptococcus faecalis*

The kanamycin resistance gene of *Streptococcus faecalis* was amplified by PCR from a known plasmid containing the gene. The nucleotide sequence of the kanamycin resistance gene of *Streptococcus faecalis* has already been elucidated (Trieu-Cuot, P. and Courvalin, P.: Gene 23 (3), 331-341 (1983)). Based on this sequence, the primers shown as SEQ ID NOS: 1 and 2 were synthesized, and PCR was performed by using them and pDG783 (Anne-Marie Guerout-Fleury et al., Gene, 167, 335-337 (1995)) as a template to amplify a DNA fragment containing the kanamycin resistance gene and its promoter.

The aforementioned DNA fragment was purified by using SUPREC02 produced by Takara Shuzo, and then completely digested with restriction enzymes HindIII and HincII and blunt-ended. The blunt-ending was performed by using Blunting Kit produced by Takara Shuzo. This DNA fragment was mixed with a DNA fragment obtained by purification and blunt-ending of an amplification product of PCR performed by using the primers shown as SEQ ID NOS: 3 and 4 and pHSG399 (refer to S. Takeshita et al, Gene, 61, 63-74 (1987)) as a template, and ligated to it. The ligation reaction was performed by using DNA Ligation Kit Ver. 2 produced by Takara Shuzo Competent cells of *Escherichia coli* JM109 (Takara Shuzo) were transformed with the ligated DNA, plated on L medium (10 g/L of Bacto trypton, 5 g/L of Bacto yeast extract, 5 g/L of NaCl, 15 g/L of agar, pH 7.2) containing 10 µg/ml of IPTG (isopropyl-β-D-thiogalactopyranoside), 40 µg/ml of X-Gal (5-bromo-4-chloro-3-indolyl-β-D-galactoside) and 25 µg/ml of kanamycin, and cultured overnight. Then, the emerged blue colonies were picked up, and separated into single colonies to obtain transformant strains.

Plasmids were prepared from the transformant strains by the alkali method (SEIBUTSU KOGAKU JIKKENSYO (Text for Bioengineering Experiments), Edited by the Society for Bioscience and Bioengineering, Japan, p.105, Baifukan, 1992), and restriction maps were prepared. One having a restriction map equivalent to that of FIG. 1 was designated as pK1. This plasmid is stably retained in *Escherichia coli*, and imparts kanamycin resistance to a host. Moreover, since it contains the lacZ' gene, it is suitably used as a cloning vector.

<2> Construction of Shuttle Vector pSFK6

Figure 2:
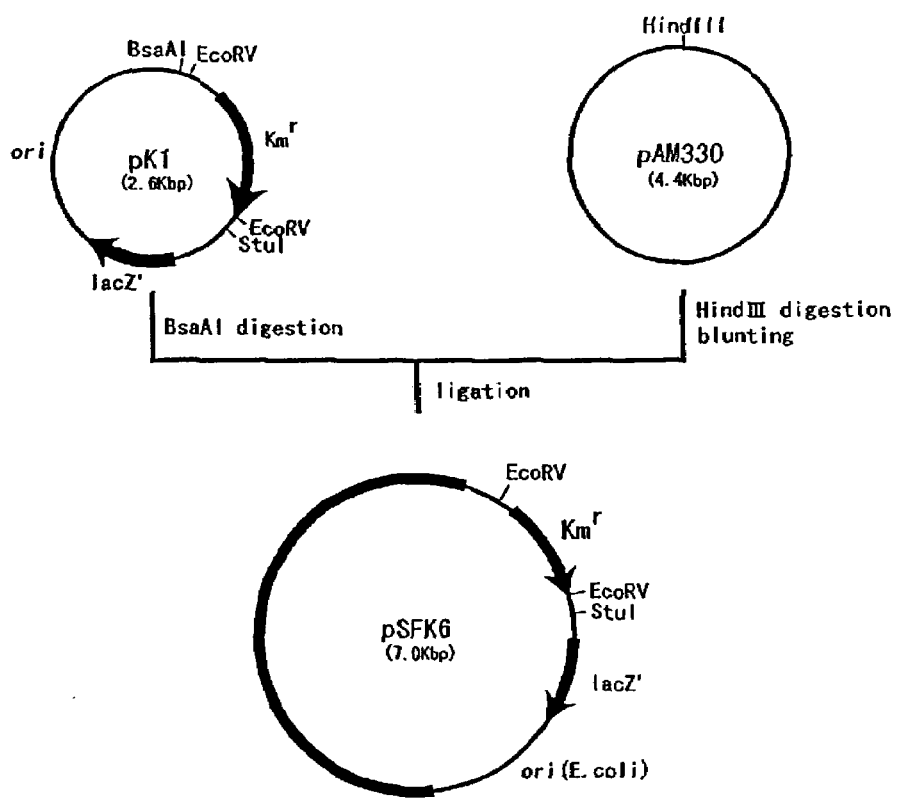
FIG. 2 shows construction process of plasmid pSFK6.

As a material for obtaining a temperature sensitive replication control region, a plasmid vector autonomously replicable in both of *Escherichia coli* cells and *coryneform* bacterium cells was prepared. The plasmid pAM330 extracted from *Brevibacterium lactofermentum* ATCC13869 (refer to Japanese Patent Publication Laid-open No. 58-67699) was completely digested with a restriction enzyme HindIII and blunt-ended. This fragment was ligated to a fragment obtained by completely digesting the aforementioned pK1 with a restriction enzyme BsaAI. *Brevibacterium lactofermentum* ATCC13869 was transformed with the ligated DNA. The transformation was performed by the electric pulse method (refer to Japanese Patent Publication Laid-open No. 2-207791). Transformants were selected on an M-CM2B plate (10 g/L of polypeptone, 10 g/L of yeast extract, 5 g/L of NaCl, 10 µg/L of biotin, 15 g/L of agar, pH 7.2) containing 25 µg/ml of kanamycin. After culture for 2 days, colonies were picked up and separated into single colonies to obtain the transformants. Plasmid DNAs were prepared from the transformants, and restriction maps were prepared. One having the same restriction map as that of FIG. 2 was designated as pSFK6. This plasmid is autonomously replicable in both of *Escherichia coli* and *coryneform* bacteria, and imparts kanamycin resistance to a host.

<3> Construction of Plasmid having Temperature Sensitive Replication Control Region pSFK6 was treated with hydroxylamine in vitro. The hydroxylamine treatment was performed according to a known method (refer to, for example, G. O. Humpherys et al., Molec. Gen. Genet., 145, 101-108 (1976)). DNA undergone the treatment was collected and used for transformation of *Brevibacterium lactofermentum* ATCC13869 strain. The transformants were selected at a low temperature (25° C.) on a CM2B plate containing 25 µg/ml of kanamycin. The emerged transformants were replicated to a similar selection plate, and cultured at an elevated temperature (34° C.). One strain that could not grow on the selection plate containing kanamycin at the elevated temperature was obtained. From this strain, a plasmid was recovered and designated as p48K.

<4> Determination of Nucleotide Sequence of Temperature Sensitive Replication Control Region Nucleotide sequences of replication control region segments in the plasmid pSFK6 having a wild-type replication control region and the plasmid p48K having a temperature sensitive replication control region were determined. The nucleotide sequences were determined on a fully automatic sequencer, ABI310 (ABI), by using DNA Sequencing Kit from ABI. As a result, it was found that there were 6 nucleotide substitutions between the wild-type replication control region and the temperature sensitive replication control region. The nucleotide sequence of the temperature sensitive replication control region segment contained in pSFK6 (total sequence derived from pAM330), which functions in *coryneform* bacteria, is shown as SEQ ID NO: 5, and the nucleotide sequence of the temperature sensitive replication control region segment contained in p48K, which functions in *coryneform* bacteria, is shown as SEQ ID NO: 7. Further, the amino acid sequences encoded by ORFs contained in these nucleotide sequences are shown as SEQ ID NOS: 6 and 8. In the temperature sensitive replication control region, the 1255th C is mutated to T, the 1534th C to T, the 1866th G to A, the 2058th G to A, the 2187th C to T and 3193rd G to A. Among these, only the mutation at 1534th position is accompanied by an amino acid mutation, and causes substitution of serine for proline.

<5> Construction of Shuttle Vectors having Temperature Sensitive Mutation

Figure 3:
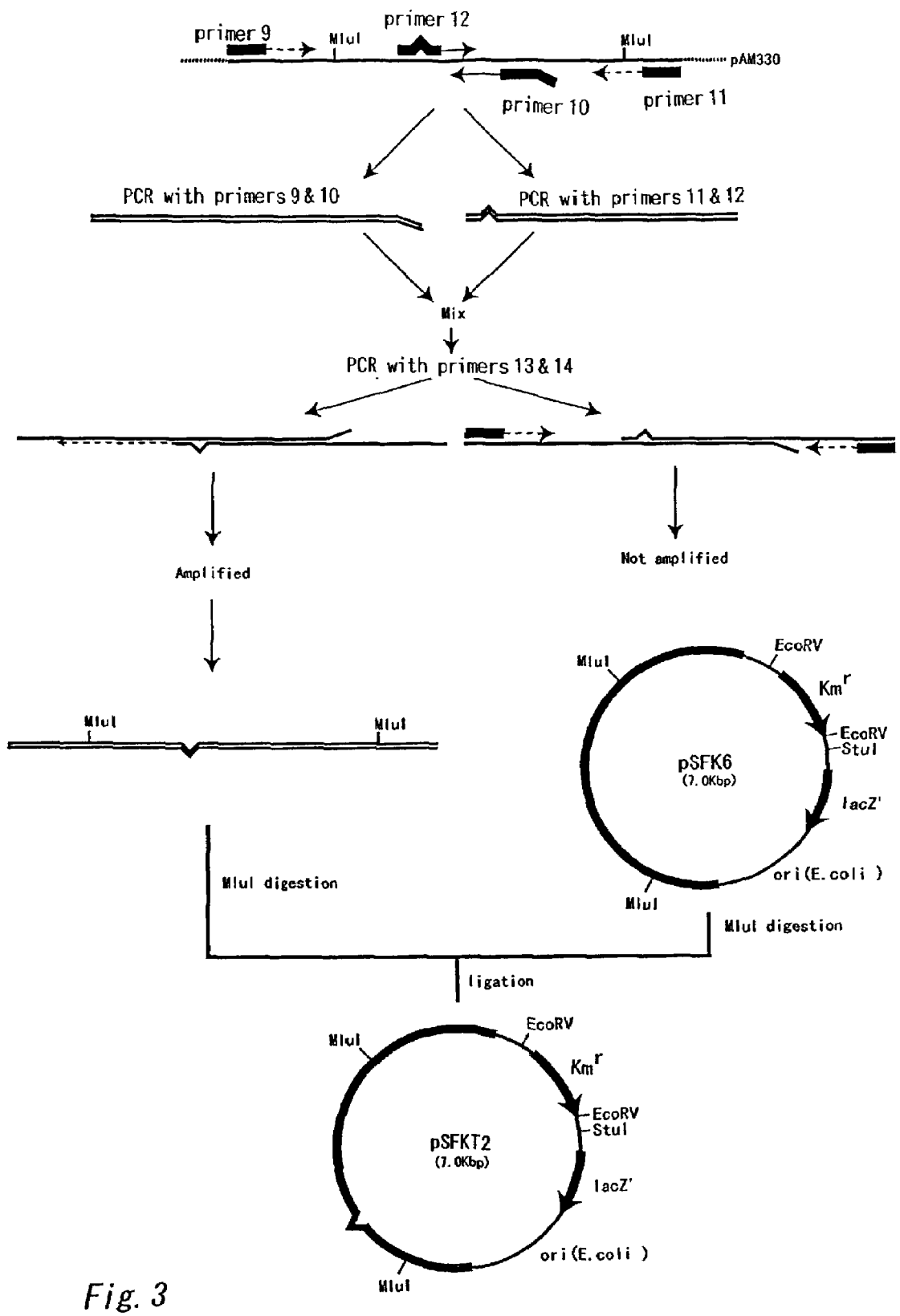
FIG. 3 shows construction process of plasmid pSFKT2.

Each one of the six mutations of p48K was introduced into a shuttle vector pSFK6 (refer to FIG. 3). The introduction of the mutations was performed by a known method (Mikaelian, I., Sergeant, A., Nucleic Acids Res., 20, 376 (1992)). Concrete procedure will be mentioned below. In order to introduce the mutation of 3193rd G to A, PCR was performed by using a combination of the primers shown as SEQ ID NOS: 9 and 10, and a combination of the primers shown as SEQ ID NOS: 11 and 12, and pAM330 as a template. Each of the obtained amplification products was purified by subjecting them to agarose gel electrophoresis, and collecting them from the gel. The collection of the DNA fragments from the gel was performed by using EASYTRAP Ver. 2 (Takara Shuzo). The purified DNAs were mixed in a molar ratio of 1:1 and used as a template for PCR performed by using the primers shown SEQ ID NOS: 13 and 14. The amplification product was fully digested with a restriction enzyme MluI and subjected to agarose gel electrophoresis to recover a DNA fragment of about 3.2 kb. Similarly, pSFK6 was also completely digested with a restriction enzyme MluI and subjected to agarose gel electrophoresis to recover a DNA fragment of about 3.8 kb. The obtained DNA fragments were mixed and ligated, and used to transform competent cells of *Escherichia coli* JM109 (Takara Shuzo). The cells were applied on L medium containing 25 µg/ml of kanamycin and cultured overnight. The emerged colonies were picked up and separated into single colonies to obtain transformant strains. A plasmid was prepared from the transformant strains by the alkaline method, and the nucleotide sequence of the plasmid was determined to confirm that the 1534th C in the sequence shown as SEQ ID NO: 17 was mutated to T. This plasmid was designated as pSFKT2 (FIG. 3).

Example 2

Cloning of argR Gene and Amplification Effect thereof in *coryneform* Bacterium

PCR was performed by using chromosome DNA of the *Brevibacterium flavum* wild strain 2247 (AJ14067) as a template and the oligonucleotides having the nucleotide sequences shown as SEQ ID NO: 15 (sequence of the nucleotide numbers 1717-1741 in SEQ ID NO: 17) and SEQ ID NO: 16 (sequence complementary to the sequence of the nucleotide numbers 2386-2362 in SEQ ID NO: 17) as primers. PCR was performed for 30 cycles each consisting of reactions at 98° C. for 10 seconds, 58° C. for 1 minute and 72° C. for 3 minutes by using Pyrobest DNA polymerase (Takara Shuzo). The obtained amplified fragment was inserted into the SmaI site of the shuttle vector pSFK6 obtained in Example 1 to obtain a plasmid pWR autonomously replicable in *coryneform* bacteria.

In order to investigate the amplification effect of argR gene in L-arginine producing *coryneform* bacteria, pWR was introduced into an L-arginine producing *Brevibacterium flavum*, the AJ11345 strain (FERM BP-6894). The plasmid was introduced by the electric pulse method (Japanese Patent Laid-open No. 2-207791). A transformant was selected as a kanamycin resistant strain on CM2G agar medium (containing 5 g of glucose, 5 g of NaCl and 15 g of agar in 1 L of pure water, pH 7.2) containing 25 µg/ml of kanamycin to obtain AJ11345/pWR. As a control, pSFK6 was similarly introduced into the AJ11345 strain to obtain a transformant AJ11345/pSFK6.

Each of the aforementioned strains was plated on an agar medium containing 0.5 g/dl of glucose, 1 g/dl of polypeptone, 1 g/dl of yeast extract and 0.5 g/dl of NaCl, and cultured at 31.5° C. for 20 hours. One loop of the obtained cells were inoculated into a medium containing 4 g/dl of glucose, 6.5 g/dl of ammonium sulfate, 0.1 g/dl of $KH_2PO_4$, 0.04 g/dl of $MgSO_4$, 0.001 g/dl of $FeSO_4$, 0.001 g/dl of $MnSO_4$, 5 µg/dl of vitamin $B_1$, 5 µg/dl of biotin and soybean protein hydrolysate (45 mg/dl as N amount), and cultured in a flask at 31.5° C. for 50 hours with shaking. Accumulation amount of L-arginine (concentration, g/dl) in each culture broth was measured. The results are shown in Table 1. As a result, the argR-amplified strain hardly accumulated L-arginine. This demonstrated that the argR gene product functioned as an arginine repressor.

TABLE 1

| Strain | L-Arginine accumulation amount (g/dl) |
|---|---|
| AJ11345/pSFK6 | 1.3 |
| AJ11345/pWR | 0.2 |

The result of nucleotide sequencing for the inserted fragment cloned into pWR is shown as SEQ ID NO: 17. An amino acid sequence that may be encoded by that nucleotide sequence is shown as SEQ ID NO: 18.

Example 3

Construction of argR-disrupted Strain of *coryneform* Bacterium and Effect of Deletion of Arginine Repressor <1> Construction of Plasmid for argR Disruption PCR was performed by using chromosome DNA of a *Brevibacterium flavum* wild strain, 2247 strain (AJ14067), as a template and the oligonucleotides having the nucleotide sequences shown as SEQ ID NO: 19 (sequence of the nucleotide numbers 4-28 in SEQ ID NO: 17) and SEQ ID NO: 20 (sequence complementary to the sequence of the nucleotide numbers 4230-4211 in SEQ ID NO: 17) as primers (Primers 3 and 4). PCR was performed for 30 cycles each consisting of reactions at 98° C. for 10 seconds, 58° C. for 1 minute and 72° C. for 3 minutes by using Pyrobest DNA polymerase (Takara Shuzo). The obtained amplified fragment was inserted into the SmaI site in the multicloning site of cloning vector pHSG399.

In order to delete the whole ORF considered to encode the arginine repressor from the inserted DNA fragment, PCR was performed by using the oligonucleotides having the nucleotide sequences shown as SEQ ID NO: 21 (sequence of the nucleotide numbers 2372-2395 in SEQ ID NO: 17) and SEQ ID NO: 22 (sequence complementary to the sequence of the nucleotide numbers 1851-1827 in SEQ ID NO: 17) as primers (Primers 5 and 6) and pHSG399 inserted with the amplified fragment as a template. pssER was constructed by self-ligation of the PCR product.

Then, a fragment obtained by digesting pssER with restriction enzymes SmaI and SalI and the temperature sensitive plasmid pSFKT6 obtained in Example 1 and digested with SmaI and SalI were ligated to obtain a plasmid pssERT for argR disruption whose autonomous replication ability in coryneform bacteria became temperature sensitive.

<2> Acquisition of Arginine Repressor Deficient Strain of coryneform Bacterium by Homologous Recombination The plasmid pssERT obtained as described above was introduced into a Brevibacterium lactofermentum wild strain, 2256 (ATCC13869). The plasmid was introduced by the electric pulse method (Japanese Patent Laid-open No. 2-207791). Because this plasmid showed temperature sensitive autonomous replication ability in Brevibacterium lactofermentum, only strains in which this plasmid was incorporated into the chromosome by homologous recombination could be selected as kanamycin resistant strains at 34° C., which was a temperature that did not allow replication of the plasmid. Strains in which the plasmid for argR disruption was incorporated into a chromosome were selected as kanamycin resistant strains on a CM2G plate (containing 10 g/L of polypeptone, 10 g/L of yeast extract, 5 g/L of glucose, 5 g/L of NaCl and 15 g/L of agar in 1 L of water, pH 7.2) containing 25 µg/ml of kanamycin. At this stage, the normal argR gene derived from the chromosome and the argG gene derived from the plasmid in which ORF was deleted were present in tandem at the both sides of the plasmid portion on the chromosome.

Then, the recombinant strains were allowed to cause homologous recombination again, and strains that became kanamycin sensitive were selected at 34° C., which was a temperature that did not allow the plasmid replication, as strains in which one of the argR genes was dropped. These strains included strains in which the normal argR gene remained on the chromosome and strains in which the disrupted argR gene remained on the chromosome. From these strains, a strain having only the disrupted argR gene was selected. An argR gene on the chromosome could be determined to be the disrupted type by preparing chromosome of a strain that became kanamycin sensitive at 34° C., performing PCR utilizing the chromosome as a template and the oligonucleotides having the nucleotide sequences shown as SEQ ID NOS: 19 and 20 as primers (Primers 3 and 4), and confirming that the PCR product was shorter by about 600 bp than that obtained by similarly performing PCR utilizing chromosome derived from the parent strain as a template.

Direct sequencing of the PCR product of the argR-disrupted strain selected as described above was performed to confirm that the argR gene was disrupted as desired, and thus 2256ΔR stain was obtained.

<3> Production of L-arginine Using argR-disrupted Strain

The 2256ΔR strain was plated on an agar medium containing 0.5 g/dl of glucose, 1 g/dl of polypeptone, 1 g/dl of yeast extract and 0.5 g/dl of NaCl and cultured at 31.5° C. for 20 hours. One loop of the obtained cells were inoculated into a medium containing 3 g/dl of glucose, 6.5 g/dl of ammonium sulfate, 0.1 g/dl of $KH_2PO_4$, 0.04 g/dl of $MgSO_4$, 0.001 g/dl of $FeSO_4$, 0.001 g/dl of $MnSO_4$, 300 µg/dl of vitamin $B_1$, 200 µg/dl of biotin and soybean protein hydrolysate (165 mg/dl as N amount) and adjusted to pH 7.0 with NaOH, and cultured at 31.5° C. for 24 hours as seed culture.

The above seed culture broth was inoculated in an amount of 1 ml into a medium containing 4 g/dl of glucose, 6.5 g/dl of ammonium sulfate, 0.5 g/dl of $KH_2PO_4$, 0.04 g/dl of $MgSO_4$, 0.001 g/dl of $FeSO_4$, 0.01 g/dl of $MnSO_4$, 5 µg/dl of vitamin $B_1$, 5 µg/dl of biotin and soybean protein hydrolysate (45 mg/dl as N amount) and adjusted to pH 7.0 with KOH, and cultured in a flask at 31.5° C. for 50 hours with shaking. Accumulation amount of L-arginine (concentration, mg/dl) in culture broth of each strain was measured. The results are shown in Table 2. As a result, the argR-disrupted strain accumulated L-arginine in a markedly larger amount compared with the parent strain.

TABLE 2

| Strain | L-Arginine accumulation amount (mg/dl) |
| --- | --- |
| 2256 | 0 |
| 2256ΔR | 200 |

Example 4

Effect of Amplification of lysE in Arg Producing coryneform Bacterium

<1> Construction of Plasmid Carrying lysE Gene

In order to confirm the effect of amplification of lysE gene in the aforementioned strain, a plasmid containing the lysE gene and a replication control region of coryneform bacteria was constructed.

The plasmid pHK4 (refer to Japanese Patent Laid-open Publication No. 5-7491) containing the replication origin of the plasmid pHM1519 (Agric. Biol. Chem., 48, 2901-2903 (1984)) that had been already obtained and was autonomously replicable in coryneform bacteria was digested with restriction enzymes BamHI and KpnI to obtain a gene fragment containing the replication origin. The obtained fragment was blunt-ended by using DNA Blunting Kit (Takara Shuzo) and inserted into the KpnI site of pHSG399 using a KpnI linker (Takara Shuzo) to obtain a shuttle vector pKC for Escherichia coli and coryneform bacteria.

Figure 4:
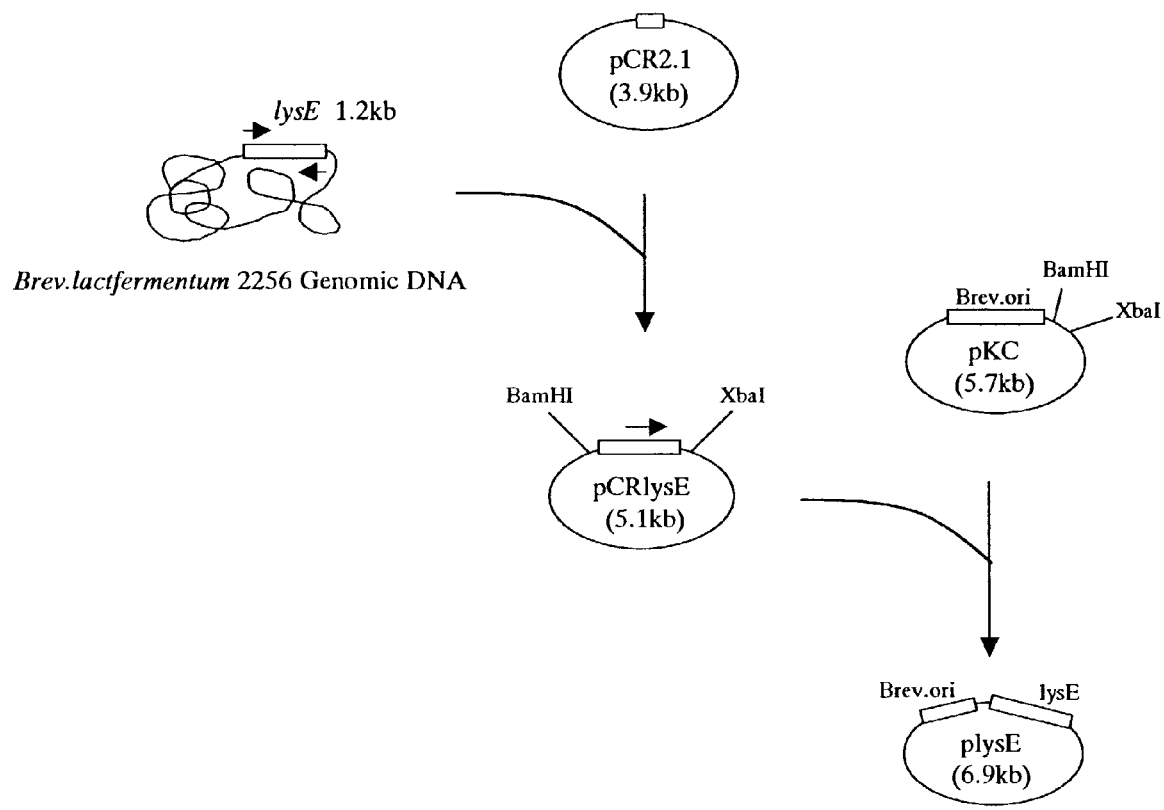
FIG. 4 shows construction process of plasmid plysE containing lysE.

Then, PCR was performed by using chromosomal DNA of a Brevibacterium lactofermentum wild strain, 2256 strain, as a template and oligonucleotides having the nucleotide sequences shown as SEQ ID NO: 23 (sequence of the nucleotide numbers 681-703 in SEQ ID NO: 25) and SEQ ID NO: 24 (sequence complementary to the sequence of the nucleotide numbers 1841-1863 in SEQ ID NO: 25) as primers to amplify the DNA fragment containing the lysE gene. PCR was performed by using TaKaRa Ex Taq (Takara Shuzo) as DNA polymerase for 30 cycles each consisting of reactions at 98° C. for 30 seconds, 55° C. for 15 seconds and 72° C. for 2 minutes. The obtained amplified fragment was inserted into TA cloning vector pCR2.1 (Invitrogen) to obtain pCRlysE. Furthermore, a gene fragment was excised with restriction enzymes BamHI and XbaI so as to contain the insert fragment and ligated to the BamHI and XbaI site of pKC to construct a plasmid plysE carrying lysE derived from Brevibacterium lactofermentum. This construction process is shown in FIG. 4.

<2> Confirmation of Effect of lysE Gene Amplification in 2256 Strain and 2256ΔR Strain The plasmid plysE prepared as described above was introduced into the *Brevibacterium lactofermentum* 2256 strain and 2256ΔR strain. The plasmid was introduced by using the electric pulse method (Japanese Patent Laid-open Publication No. 2-207791). Transformants were selected on a CM2G medium plate (containing 10 g of polypeptone, 10 g of yeast extract, 5 g of glucose, 5 g of NaCl and 15 g of agar in 1 L of pure water, pH 7.2) containing 5 μg/ml of chloramphenicol as chloramphenicol resistant strains. These transformants were cultured in flasks in the same manner as described above, and the amounts of L-arginine accumulation were measured. The results are shown in Table 3.

TABLE 3

| Strain | L-Arginine accumulation amount (mg/dl) |
|---|---|
| 2256 | 0 |
| 2256/plysE | 0 |
| 2256ΔR | 200 |
| 2256ΔR/plysE | 600 |

Example 5

Confirmation of Amplification Effect Combined with Amplification of L-arginine Biosynthetic Pathway Gene <1> Preparation of Plasmid Carrying L-arginine Biosynthetic Pathway Gene Furthermore, in order to confirm the amplification effect of L-arginine biosynthetic pathway genes, argC, J, B, F, G and H, in the aforementioned strain, a plasmid containing the argCJBDFGH gene and a replication control region of *coryneform* bacterium was constructed.

The plasmid pHK4 (Japanese Patent Laid-open Publication No. 5-7491) was digested with restriction enzymes BamHI and KpnI to obtain a gene fragment containing a replication control region of *coryneform* bacterium. The obtained fragment was blunt-ended by using DNA Blunting Kit (Takara Shuzo) and inserted into the SalI site of pHSG399 using a SalI linker (Takara Shuzo) to obtain a shuttle vector pSAC4 for *Escherichia coli* and *coryneform* bacteria.

Figure 5:
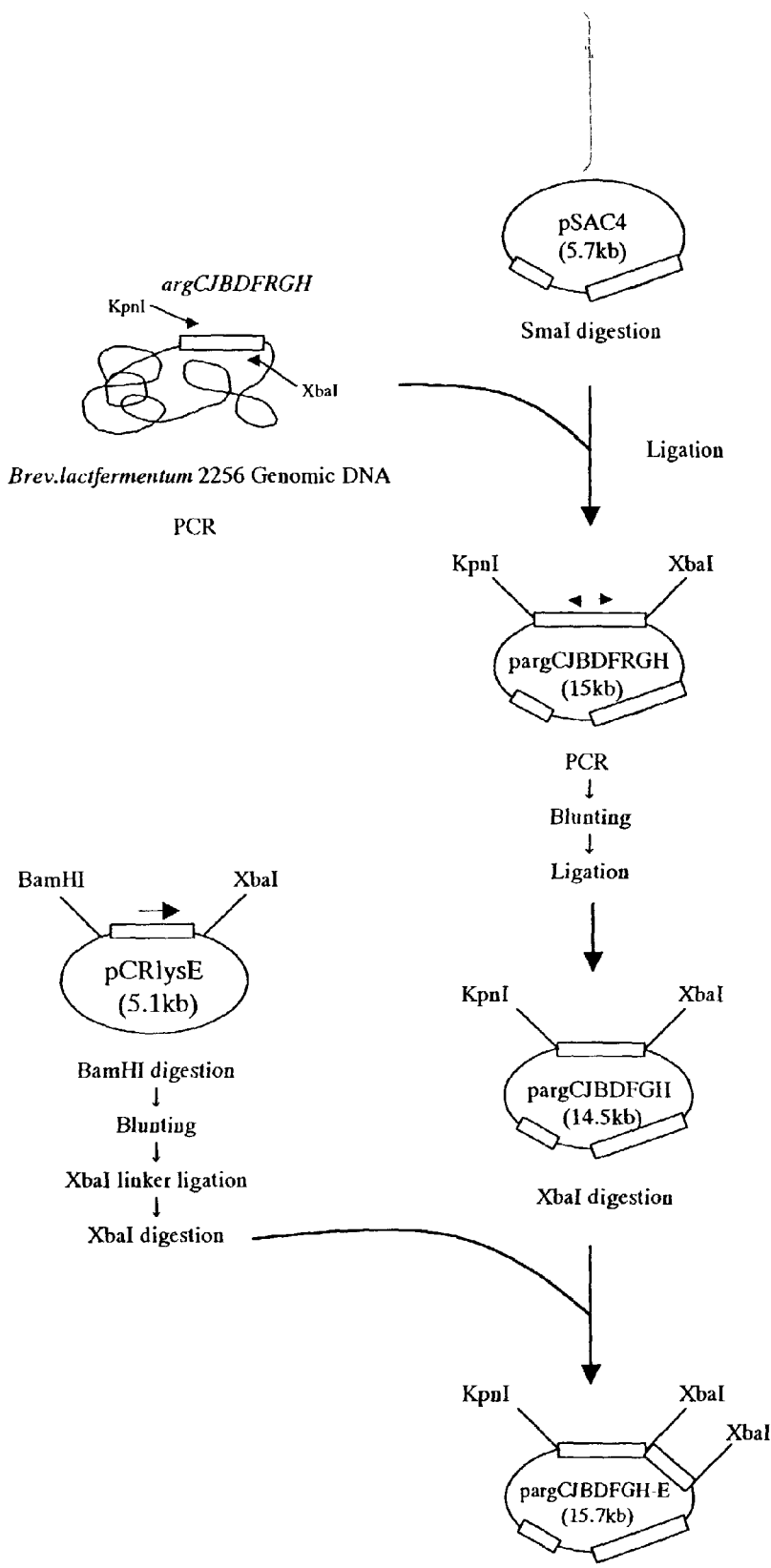
FIG. 5 shows construction processes of plasmid pargCJB-DFGH containing a gene for L-arginine biosynthesis enzyme and not containing argR gene and plasmid pargCJB-DFGH-E containing lysE and a gene for L-arginine biosynthesis enzyme.

Then, PCR was performed by using chromosomal DNA of the *Brevibacterium lactofermentum* wild strain, 2256 strain, as a template and oligonucleotides having the nucleotide sequences shown as SEQ ID NO: 27 and 28 as primers to amplify the DNA fragment containing the argCJBD-FRGH gene. PCR was performed by using TaKaRa LA Taq (Takara Shuzo) as DNA polymerase for 30 cycles each consisting of reactions at 98° C. for 30 seconds, 55° C. for 15 seconds and 72° C. for 6 minutes. The obtained amplified fragment was blunt-ended, and then inserted into the SmaI site of pSAC4 to obtain a plasmid pargCJBDFRGH carrying argCJBDFRGH derived from *Brevibacterium lactofermentum*. Furthermore, PCR was performed by using this plasmid as a template and oligonucleotides having the nucleotide sequences shown as SEQ ID NO: 29 and 30 as primers for amplifying the outside of ORF of the argR gene. PCR was performed by using TaKaRa LA Taq (Takara Shuzo) as DNA polymerase, and repeating a cycle consisting of reactions at 98° C. for 20 seconds and 68° C. for 15 seconds for 30 cycles, which was followed by a reaction at 72° C. for 10 minutes. The obtained amplified fragment was blunt-ended and self-ligated by using TaKaRa Ligation Kit ver. 2 to construct a plasmid pargCJBDFGH not carrying the argR gene. This construction process is shown in FIG. 5.

<2> Confirmation of Amplification Effect of L-arginine Biosynthetic Pathway Gene pargCJBDFGH was introduced into the 2256 strain to obtain a transformant 2256/pargCJBDFGH. The 2256 strain and 2256/pargCJBDFGH strain were cultured in flasks in the same manner as described above, and the amounts of L-arginine accumulation were measured. The results are shown in Table 4.

TABLE 4

| Strain | L-Arginine accumulation (mg/dl) |
|---|---|
| 2256 | 0 |
| 2256/pargCJBDFGH | 300 |

<3> Confirmation of Effect of Combined Amplification of L-arginine Biosynthetic Pathway Gene and lysE Gene In order to confirm the effect of amplifying an L-arginine biosynthetic pathway gene and lysE gene in combination, a DNA fragment containing the lysE gene was excised from the aforementioned plasmid pCRlysE by digestion with BamHI, blunt-ended by using DNA Blunting Kit (Takara Shuzo) and then inserted into the XbaI site of the plasmid pargCJBDFGH by using an XbaI linker to construct a plasmid pargCJBDFGH-E. This construction process is shown in FIG. 5. This plasmid was introduced into the 2256 strain. The cells of the strain were cultured in a flask in the same manner as described above, and the amount of L-arginine accumulation was measured. The results are shown in Table 5.

TABLE 5

| Strain | L-Arginine accumulation amount (mg/dl) |
|---|---|
| 2256 | 0 |
| 2256/pargCJBDFGH | 200 |
| 2256/plysE | 0 |
| 2256/pargCJBDFGH-E | 400 |

Example 6

Effect of lysE Amplification in Arg Producing Strain of *Escherichia coli*

<1> Construction of Plasmid pRSlysE Carrying lysE Gene

A plasmid pRSlysE for lysE expression was constructed by using a known plasmid pRS (refer to International Patent Publication in Japanese No. 3-501682) (FIG. 6). pRS is a plasmid having the vector segment of the pVIC40 plasmid (International Patent Publication WO90/04636, International Patent Publication in Japanese No. 3-501682) and obtained from pVIC40 by deleting a DNA region coding for the threonine operon possessed by the plasmid. The plasmid pVIC40 was derived from a broad host spectrum vector plasmid pAYC32 (Chistorerdov, A. Y., Tsygankov, Y. D., Plasmid, 1986, 16, 161-167), which was a derivative of RSF1010.

Figure 6:
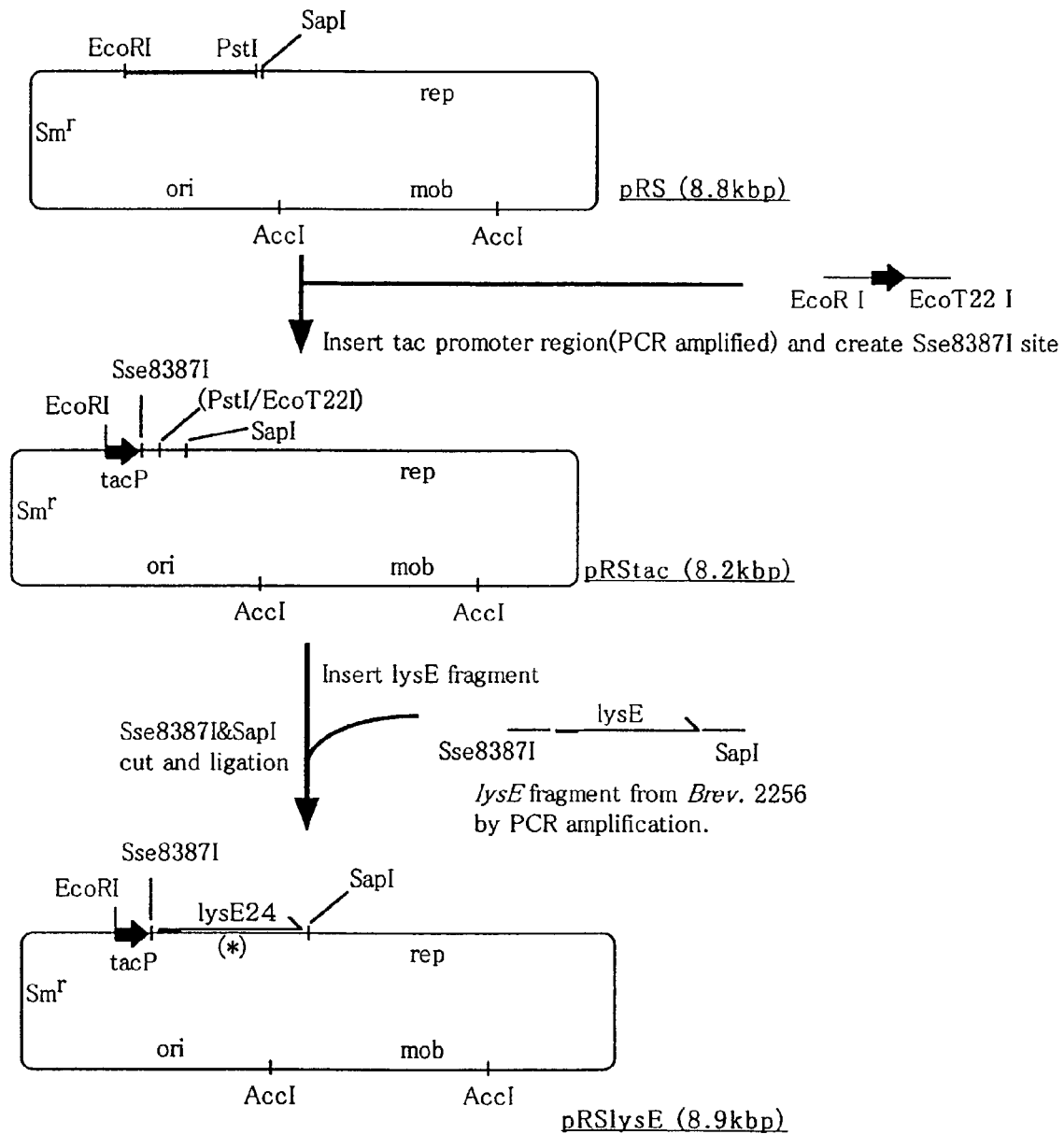
FIG. 6 shows constructions of pRStac having tac promoter and plasmid pRSlysE obtained by inserting the lysE gene into the plasmid pRStac.

First, a plasmid pRStac having the tac promoter was constructed from pRS according to the scheme shown in FIG. 6. First, the pRS vector was digested with restriction enzymes EcoRI and PstI and added with a phenol/chloroform solution and mixed with it to terminate the reaction. After the reaction mixture was centrifuged, the upper layer was collected, and DNAs were collected by ethanol precipitation and separated on 0.8% agarose gel. A DNA fragment of 8 kilobase pairs (henceforth abbreviated as "kbp") was collected by using EASY TRAP Ver. 2 (DNA collection kit, Takara Shuzo). On the other hand, the tac promoter region was amplified by PCR using the pRK223-3 plasmid (expression vector, Pharmacia) as a template and the primers shown as SEQ ID NOS: 31 and 32 (a cycle consisting of denaturation at 94° C. for 20 seconds, annealing at 55° C. for 30 seconds and extension reaction at 72° C. for 60 seconds was repeated for 30 cycles). Pyrobest DNA polymerase (Takara Shuzo) was used for PCR. The DNA fragment containing the amplified tac promoter was purified by using PCR prep (Promega) and then digested at the restriction enzyme sites preliminarily designed in the primers, i.e., at EcoRI and EcoT22I sites. Then, the reaction mixture was added with a phenol/chloroform solution and mixed with it to terminate the reaction. After the reaction mixture was centrifuged, the upper layer was collected and DNAs were collected by ethanol precipitation and separated on 0.8% agarose gel. A DNA fragment of about 0.15 kbp was collected by using EASY TRAP Ver. 2.

The digestion product of the pRS vector and the tac promoter region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies emerged on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes to obtain pRStac. A plasmid in which the transcription directions of the streptomycin resistance gene on the pRS vector and the tac promoter were the same was selected as pRStac. pRStac obtained as described above was digested with Sse8387I (Takara Shuzo) and SapI (New England Biolabs), added with a phenol/chloroform solution and mixed with it to terminate the reaction. After the reaction mixture was centrifuged, the upper layer was collected and DNAs were collected by ethanol precipitation and separated on 0.8% agarose gel to obtain a DAN fragment of about 9.0 kbp.

The lysE gene fragment was also amplified by PCR using chromosome extracted from the *Brevibacterium lactofermentum* 2256 strain (ATCC13869) as a template and the primers shown as SEQ ID NOS: 33 and 34 (denaturation at 94° C. for 20 seconds, annealing at 55° C. for 30 seconds and extension reaction at 72° C. for 90 seconds). Pyrobest DNA polymerase (Takara Shuzo) was used for PCR. The obtained fragment was purified by using PCR prep (Promega) and then digested with restriction enzymes Sse8387I and SapI. The reaction mixture was added with a phenol/chloroform solution and mixed with it to terminate the reaction. After the reaction mixture was centrifuged, the upper layer was collected and DNAs were collected by ethanol precipitation and further collected from 0.8% agarose gel.

The digestion product of the pRStac vector and the lysE gene region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies emerged on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes and determination of nucleotide sequence to obtain pRSlysE. In pRSlysE, the lysE gene was positioned so that its transcription direction should be the same as that of the tac promoter.

<2> Construction of Plasmid pGEM5 Carrying yggA Gene

The whole nucleotide sequence of chromosomal DNA of *Escherichla coli* K-12 strain had been already determined (Science, 277, 1453-1474, 1997). Based on this reported nucleotide sequence, a DNA fragment containing the yggA gene was amplified by PCR using the primers shown as SEQ ID NOS: 35 and 36 and chromosomal DNA of *Escherichia coli* MG1655 strain as a template. The primer shown as SEQ ID NO: 35 had a sequence complementary to the sequence of nucleotide the numbers 9606-9626 in the nucleotide sequence registered at GenBank with an accession number of AE000375, and the primer shown as SEQ ID NO: 36 had the sequence of the nucleotide numbers 8478-8498 of the same.

The chromosomal DNA of *Escherichia coli* MG1655 strain was prepared in a conventional manner. PCR was performed under the standard conditions described in PCR Protocols, Current Methods and Applications, White, B. A., ed., Humana Press, Totowa, N.J., 1993.

The obtained PCR product was purified in a conventional manner and cloned into the pGEM-T vector (Promega). The obtained plasmid was designated as pGEM5.

<3> Confirmation of Effect of lysE Gene Amplification in Arg Producing Strain of *Escherichia coli*

The plasmids pRSlysE and pGEM5 constructed as described above were introduced into an Arg producing strain of *Escherichia coli*, 237 strain, respectively. The 237 strain was a mutant strain resistant to a pyrimidine analogue, 6-azauracil, which was derived from *Escherichia coli* K12 ilvA::Tn5 by using 1-methyl-3-nitro-1-nitrosoguanidine. This strain was deposited at the All-Russian Collection for Industrial Microorganisms (VKPM)(1, Dorozhny Proezd., 1, 113545, Moscow, Russia) with the designation of VKPM B-7925. Transformation was performed in a conventional manner.

To confirm L-arginine producing ability of the obtained transformant, the transformant was evaluated by culturing it (32° C., 3 days, culture with shaking). Composition of the medium used was as follows (unit: g/L): 60 g/L of glucose, 35 g/L of $(NH_4)_2SO_4$, 5 g/L of yeast extract, 2 g/L of $KH_2PO_4$, 1 g/L of $MgSO_4 \cdot 7H_2O$ and 25 g/L of $CaCO_3$. The amount of L-arginine accumulated in the medium was measured by a known method, and the results are shown in Table 6.

TABLE 6

| Strain | L-Arginine accumulation amount (mg/dl) |
| --- | --- |
| 237 | 450 |
| 237/pRSlysE | 890 |
| 237/pGEM5 | 600 |

The amount of accumulated L-arginine was improved by the introduction of the plasmid pRSlysE for amplifying lysE. The improvement degree of higher level was obtained compared with that obtained with pGEM for amplifying yggA, which had hitherto been reported as an L-arginine secretion factor.

(Explanation of Sequence Listing)
SEQ ID NO: 1: Primer for amplification of kanamycin resistance gene of *Streptococcus faecalis*
SEQ ID NO: 2: Primer for amplification of kanamycin resistance gene of *Streptococcus faecalis*
SEQ ID NO: 3: Primer for amplification of vector segment of pHSG399
SEQ ID NO: 4: Primer for amplification of vector segment of pHSG399
SEQ ID NO: 5: Nucleotide sequence of replication control region of pSFK6
SEQ ID NO: 6: Amino acid sequence that may be encoded by ORF in pSFK6
SEQ ID NO: 7: Nucleotide sequence of replication control region of p48K
SEQ ID NO: 8: Amino acid sequence that may be encoded by ORF in p48K
SEQ ID NO: 9: Primer for 1st PCR for introducing mutation of 1534th C to T into pSFK6
SEQ ID NO: 10: Primer for 1st PCR for introducing mutation of 1534th C to T into pSFK6
SEQ ID NO: 11: Primer for 1st PCR for introducing mutation of 1534th C to T into pSFK6
SEQ ID NO: 12: Primer for 1st PCR for introducing mutation of 1534th C to T into pSFK6
SEQ ID NO: 13: Primer for 2nd PCR for introducing mutation of 1534th C to T into pSFK6
SEQ ID NO: 14: Primer for 2nd PCR for introducing mutation of 1534th C to T into pSFK6
SEQ ID NO: 15: Primer for argR gene amplification
SEQ ID NO: 16: Primer for argR gene amplification
SEQ ID NO: 17: Nucleotide sequence of DNA fragment containing argR gene
SEQ ID NO: 18: Amino acid sequence that may be encoded by the above DNA fragment
SEQ ID NO: 19: Primer for argR gene amplification
SEQ ID NO: 20: Primer for argR gene amplification
SEQ ID NO: 21: Primer for amplifying portions other than argR gene ORF of plasmid containing argR gene
SEQ ID NO: 22: Primer for amplifying portions other than argR gene ORF of plasmid containing argR gene
SEQ ID NO: 23: Primer for lysE gene amplification
SEQ ID NO: 24: Primer for lysE gene amplification
SEQ ID NO: 25: Nucleotide sequence of DNA fragment containing lysG and lysE genes of *Corynebacterium glutamicum* (GenBank x96471)
SEQ ID NO: 26: Amino acid sequence encoded by lysE
SEQ ID NO: 27: Primer for amplifying DNA fragment containing argC to argH genes
SEQ ID NO: 28: Primer for amplifying DNA fragment containing argC to argH genes
SEQ ID NO: 29: Primer for amplifying outside of argR ORF
SEQ ID NO: 30: Primer for amplifying outside of argR ORF
SEQ ID NO: 31: Primer for tac promoter amplification
SEQ ID NO: 32: Primer for tac promoter amplification
SEQ ID NO: 33: Primer for lysE gene amplification
SEQ ID NO: 34: Primer for lysE gene amplification
SEQ ID NO: 35: Primer for yggA gene amplification
SEQ ID NO: 36: Primer for yggA gene amplification

What is claimed is:

1. A method for producing L-arginine comprising culturing a *coryneform* bacterium, which has L-arginine producing ability and has been transformed with a polynucleotide that encodes the LysE protein having the amino acid sequence of SEQ ID NO: 26, in a medium to produce and accumulate L-arginine in the medium, and collecting the L-arginine from the medium, wherein said *coryneform* bacterium comprises a polynucleotide that encodes an arginine repressor having the amino acid sequence of SEQ ID NO: 18 which has been disrupted and overproduces L-arginine as compared to the unmodified *coryneform* bacterium.

2. The method according to claim 1, wherein the *coryneform* bacterium belongs to the genus *Brevibacterium*.

3. A method for producing L-arginine comprising culturing a *coryneform* bacterium, which has L-arginine producing ability and has been transformed with a polynucleotide that encodes the LysE protein having the amino acid sequence of SEQ ID NO: 26, in a medium to produce and accumulate L-arginine in the medium, and collecting the L-arginine from the medium, wherein intracellular activity of enzymes in the L-arginine biosynthetic pathway comprising argCJBDFGH products has been enhanced in said *coryneform* bacterium and said *coryneform* bacterium overproduces L-arginine as compared to the unmodified *coryneform* bacterium.

4. The method according to claim 3, wherein the bacterium has been transformed with polynucleotides encoding the argCJBDFGH products, whereby the activity of the argCJBDFGH products has been enhanced as compared to the unmodified *coryneform* bacterium.

5. The method according to claim 3, wherein the *coryneform* bacterium belongs to the genus *Brevibacterium*.

* * * * *